(12) United States Patent
Gavardinas et al.

(10) Patent No.: US 7,728,150 B2
(45) Date of Patent: Jun. 1, 2010

(54) BICYCLIC SUBSTITUTED INDOLE-DERIVATIVE STEROID HORMONE NUCLEAR RECEPTOR MODULATORS

(75) Inventors: Konstantinos Gavardinas, Monrovia, IN (US); Prabhakar Kondaji Jadhav, Zionsville, IN (US); Minmin Wang, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 934 days.

(21) Appl. No.: 10/598,330

(22) PCT Filed: Feb. 18, 2005

(86) PCT No.: PCT/US2005/005240

§ 371 (c)(1),
(2), (4) Date: Aug. 24, 2006

(87) PCT Pub. No.: WO2005/092854

PCT Pub. Date: Oct. 6, 2005

(65) Prior Publication Data

US 2007/0185161 A1    Aug. 9, 2007

Related U.S. Application Data

(60) Provisional application No. 60/549,754, filed on Mar. 3, 2004.

(51) Int. Cl.
*C07D 215/38* (2006.01)
(52) U.S. Cl. .............. 548/454; 548/463; 548/511
(58) Field of Classification Search ............ 548/454, 548/463, 511
See application file for complete search history.

(56) References Cited

U.S. PATENT DOCUMENTS 3,886,165 A   5/1975   Wu et al.
5,440,033 A   8/1995   Berger et al.
2005/0222201 A1*   10/2005   Birkinshaw et al. ......... 514/312

FOREIGN PATENT DOCUMENTS

| JP | 1987294679 | | 12/1987 |
| WO | WO 02/16348 A1 | | 2/2002 |
| WO | WO 02/28832 A2 | | 4/2002 |
| WO | WO 03/078394 A1 | | 9/2003 |
| WO | WO2004/067529 | * | 8/2004 |
| WO | WO 2004/067529 A1 | | 8/2004 |

OTHER PUBLICATIONS

Chemical Abstracts Registry No. 855653-69-9, 2007.
Hiyoshizo Kotsuki et al., High-Pressure Organic Chemistry. 19. High-Pressure-Promoted, Silica Gel-Catalyzed Reaction of Epoxides with Nitrogen Heterocycles, *J. Org. Chem.*, 1996, 984-990, vol. 61.

* cited by examiner

*Primary Examiner*—D. Margaret Seaman
(74) *Attorney, Agent, or Firm*—Alexander Wilson

(57) ABSTRACT

The present invention provides a compound of the formula: Formula (I); or a pharmaceutically acceptable salt thereof, pharmaceutical compositions comprising an effective amount of a compound of Formula I in combination with a suitable carrier, diluent, or excipient, and methods for treating physiological disorders, particularly congestive heart disease, hypertension, and atherosclerosis, comprising administering to a patient in thereof an effective amount of a compound of Formula I. X-16125

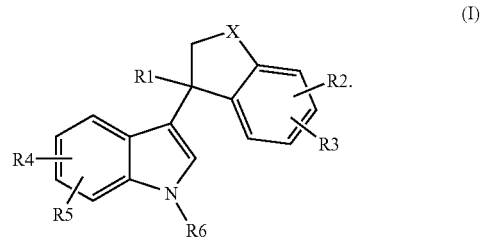

(I)

12 Claims, No Drawings

BICYCLIC SUBSTITUTED INDOLE-DERIVATIVE STEROID HORMONE NUCLEAR RECEPTOR MODULATORS

BACKGROUND OF THE INVENTION

This application is a 371 of PCT/US05/05240, Feb. 18, 2005.

Nuclear hormone receptors are an evolutionarily conserved class of intracellular receptor proteins which have been termed "ligand dependent transcription factors". Evans et al., SCIENCE, 240: 889 (1988). The nuclear hormone receptor gene superfamily encodes structurally-related receptor proteins for glucocorticoids (e.g. cortisol, corticosterone, cortisone), androgens, mineralocorticoids (e.g. aldosterone), progestins, estrogen, and thyroid hormone. Also included within this superfamily of nuclear receptors are receptor proteins for vitamin D, retinoic acid, 9-cis retinoic acid, as well as those receptors for which no cognate ligands have been identified ("orphan receptors") Ribeiro et al., Annual Rev. Med., 46:443-453 (1995). Steroid hormone receptors represent a subset of the nuclear hormone receptor superfamily. So named according to the cognate ligand which complexes with the receptor in its native state, the steroid hormone nuclear receptors include the glucocorticoid receptor (GR), the androgen receptor (AR), the mineralocorticoid receptor (MR), the estrogen receptor (ER), and the progesterone receptor (PR). Tenbaum et al., Int. J. Biochem. Cell. Bio., 29(12): 1325-1341(1997).

In contrast to membrane bound receptors, nuclear hormone receptors encounter their respective ligands following entry of the ligand into the cell. Once ligand binding occurs, the ligand-receptor complex modulates transcription of target genes within the cell nucleus. For example, most ligand-free nuclear receptors are bound in a complex with heat shock proteins (HSPs) in the cytoplasm. Following entry of circulating hormone into the cell, binding elicits a conformational change in the receptor, dissociating the receptor from the hsp. The ligand bound receptors translocate to the nucleus, where they as monomers as well as hetero- and homodimers in binding to particular hormone response elements (HREs) in the promoter regions of target genes. The HRE-receptor complex then, in turn, regulates transcription of proximally-located genes. (see Ribeiro et al., supra.). On the other hand, thyroid hormone receptors (TRs) and other non-steroid receptors such as vitamin D receptor (VDR) and retinoic acid receptors (RAR) are bound to their respective HRE in the absence of HSPs and/or cognate ligand. Hormones released from the circulation enter the cell, binding in the nucleus to these receptors which, in turn, hetero-dimerize to other nuclear receptors such as 9-cis retinoic acid (RXR). As with the steroid hormone nuclear receptors, following ligand binding, the ligand-bound receptor complex again regulates transcription of neighboring genes.

Mineralocorticoids and glucocorticoids exert profound influences on a multitude of physiological functions by virtue of their diverse roles in growth, development, and maintenance of homeostasis. The actions are mediated by the MR and GR which share approximately 94% homology in their respective DNA binding regions, and approximately 57% homology in their respective ligand-binding domains. Kino et al., J. of Endocrinology, 169, 437-445 (2001). In visceral tissues, such as the kidney and the gut, MR regulates sodium retention, potassium excretion, and water balance in response to aldosterone. In addition, MR expression in the brain appears to play a role in the control of neuronal excitability, in the negative feedback regulation of the hypothalamic-pituitary-adrenal axis, and in the cognitive aspects of behavioral performance. Castren et al., J. of Neuroendocrinology, 3, 461-466 (1993). GR, which is ubiquitously expressed in almost all tissues and organ systems, is crucial for the integrity of central nervous system function and the maintenance of cardiovascular, metabolic, and immune homeostasis. Kino et al., J. of Endocrinology, 169, 437-445 (2001).

Elevations in aldosterone levels, or excess stimulation of mineralocorticoid receptors, are linked to several physiological disorders or pathologic disease states including, Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels. Hadley, M. E., ENDOCRINOLOGY, $2^{nd}$ Ed., pp. 366-381, (1988); and Brilla et al., Journal of Molecular and Cellular Cardiology, 25 (5), pp. 563-575 (1993). Additionally, elevated aldosterone levels have been increasingly implicated with congestive heart failure (CHF). In CHF, the failing heart triggers hormonal mechanisms in other organs in response to the attending reductions in blood flow and blood pressure seen with CHF. In particular, the kidney activates the renin-angiotensin-aldosterone system (RAAS) causing an increase in aldosterone production by the adrenals which, in turn, promotes water and sodium retention, potassium loss, and further edema. Although historically it was believed that aldosterone participated in the etiology of CHF only as a result of its salt retaining effects, several recent studies have implicated elevated aldosterone levels with events in extra-adrenal tissues and organs, such as myocardial and vascular fibrosis, direct vascular damage, and baroreceptor dysfunction. Pitt et al., New Eng. J. Med., 341:709-717 (1999). These findings are particularly significant since angiotensin converting enzyme (ACE) inhibitors, which were once thought to completely abolish aldosterone production, are now believed to only transiently suppress aldosterone production which has been shown to occur in extra-adrenal tissues including the heart and vasculature. Weber, New Eng. J. Med., 341:753-755 (1999); Fardella and Miller, Annu. Rev. Nutr., 16:443-470 (1996).

The involvement of aldosterone acting via MR in CHF was confirmed in the recently completed RALES (Randomized Aldactone Evaluation Study) study. Pitt et al., New Eng. J. Med., 341:709-717 (1999). The RALES study demonstrated, that the use of Aldactone™ (spironolactone), a well-known competitive MR antagonist, in combination with standard CHF therapy, reduced cardiac related mortality by 30% and frequency of hospitalization by 35% in patients suffering from advanced CHF. However, spironolactone therapy has also been associated with attending side effects such as gastric bleeding, diarrhea, azotemia, hyperchloremic metabolic acidosis an type-4 renal tubule acidosis, nausea, gynecomastia, erectile dysfunction, hyperkalemia, and irregular menses. Thus, the mineralocorticoid receptor represents a viable target for CHF therapy either alone or in combination with conventional CHF therapies such as vasodilators (ACE inhibitors), inotropics (digoxin), diuretics, or beta blockers. Molecules, preferably non-steroids, which bind to the mineralocorticoid receptor and modulate receptor activity without the attending side effects of current therapies would be particularly desirable.

Recently, selective aldosterone blockers have also been implicated in the treatment of atherosclerosis. S. Keider, et al., *Cardiovascular Pharmacology* 41 (6), 955-963 (2003). Finally, published international PCT application WO 02/17895 discloses that aldosterone antagonists are useful in the treatment of subjects suffereing from one or more cognitive dysfunctions including, but not limited to psychoses, cognitive disorders (such as memory disturbances), mood disorders (such as depression and bipolar disorder), anxiety disorders, and personality disorders.

Glucocorticoids (e.g. cortisol, corticosterone, and cortisone), and the glucocorticoid receptor, have also been implicated in the etiology of a variety of physiological disorders or pathologic disease states. For example, cortisol hyposecretion is implicated in the pathogenesis of Addison's Disease and may result in muscle weakness, in creased melanin pigmentation of the skin, weight loss, hypotension, and hypoglycemia. On the other hand, excessive or prolonged secretion of glucocorticoids has been correlated to Cushing's Syndrome and may also result in obesity, hypertension, glucose intolerance, hyperglycemia, diabetes mellitus, osteoporosis, polyuria, and polydipsia. Hadley, M. E., ENDOCRINOLOGY, $2^{nd}$ Ed., pp. 366-381, (1988). Further, U.S. Pat. No. 6,166,013, issued Dec. 26, 2000, discloses that GR selective agents could modulate GR activity and, thus, be useful in the treatment of inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome. U.S. Pat. No. 6,166,013 also discloses that GR modulators are especially useful in disease states involving systemic inflammation such as inflammatory bowel disease, systemic lupus erythematosus, polyartitis nodosa, Wegener's granulomatosis, giant cell arthritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis; and that GR modulating compounds have been used as immunostimulants, repressors, and as wound healing and tissue repair agents.

In addition, U.S. Pat. No. 6,166,013 also discloses that GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type 1 reactive leprosy, capillary hemangiomas, contact dermatitis, a topic dermatitis, lichen planus, exfoliative dermatitis, erythema nodosum, acne, hirsutism, toxic epidermal necrolysis, erythema multiform, and cutaneous T-cell lymphoma.

Thus, it is clear that a ligand which has affinity for steroid hormone nuclear receptors, and particularly for MR and/or GR, could be used to modulate (i.e. repress, antagonize, agonize, partially antagonize, partially agonize) receptor activity and target gene expression, thereby influencing a multitude of physiological functions related to alterations in steroid hormone levels and/or steroid hormone receptor activity. In this regard, such ligands could be useful to treat a wide range of physiological disorders susceptible to steroid hormone nuclear receptor modulation.

Published literature references disclose indole derivative molecules useful in a broad range of indications from electroluminescent agents to marine anti-fouling agents. Further, indole-derivative compounds have also been disclosed as having pharmacological utility as, inter alia, serotonin 5HT-6 receptor modulators, anticoagulant agents, antiangiogenics, antiparasitics, integrin inhibitors, phospholipase inhibitors, endothelian receptor antagonists, antiarrhythmics, and dopamine antagonists. Surprisingly, however, and in accordance with the present invention, applicants have discovered a series of non-steroidal indole derivative compounds, particularly bicyclic substituted indole derivatives, with affinity for steroid hormone nuclear receptors, and particularly for MR and GR. Such compounds could modulate nuclear receptor activity and, therefore, have utility in treating physiological disorders related to alterations in steroid hormone level and/or to alterations in steroid hormone nuclear receptor activity. Furthermore, such compounds could address a long felt and continuing need for safe and effective pharmaceutical interventions without the attending side effects of steroidal-type agents. The treatment of steroid hormone related disorders is hereby furthered.

The following references describe examples of the state of the art as it relates to the present invention.

Published International PCT Application WO 96/19458 and U.S. Pat. Nos. 5,696,130; 5,994,544; 6,017,924, and 6,121,450 disclose quinoline derivative analogs as steroid hormone receptor modulators.

Published International PCT Application WO 00/06137 and U.S. Pat. No. 6,166,013 disclose triphenylmethane compounds as glucocorticoid receptor modulators.

U.S. Pat. No. 6,147,066 discloses anti-mineralocorticoid receptor compounds for use in treating drug withdrawal syndrome.

U.S. Pat. Nos. 6,008,210 and 6,093,708 disclose spirolactone compounds, such as spironolactone and epoxymexrenone, with affinity for the mineralocorticoid receptor for use in the treatment of myocardial fibrosis.

Published International PCT Application WO 02/17895 discloses that aldosterone antagonists are useful in the treatment of subjects suffereing from one or more cognitive dysfunctions.

Published International PCT Application WO 02/09683 discloses aldosterone blockers useful to treat inflammation disoders.

Published International PCT Application WO 02/051832 discloses heterocyclalkylindoles as 5HT-6 ligands.

Published International PCT Application WO 02/016348 discloses indole derivatives molecules as antiangiogenic agents.

Published International PCT Application WO 02/012227 discloses nine-, and ten-membered bicylic heteroaryl molecules as angiogenesis inhibitors.

Published International PCT Application WO 01/058893 discloses indol-3-yl propionates as integrin inhibitors.

Published International PCT Application WO 99/43672 discloses indole derivatives as phospholipase enzyme inhibitors.

Published International PCT Application WO 98/42696 and related family members disclose inhibitors of nitric oxide synthase.

Published International PCT Application WO 97/43260 and related family members disclose indole derivatives useful as endothelin receptor antagonists.

Published International PCT Application WO 96/03377 and related family members disclose heterocyclic compounds useful as allosteric effectors of muscarinic receptors.

European Patent EP683166 discloses 1-(3-indolylalkyl)-4-(3-indolyl)piperidines as dopamine agonists or antagonists.

Japanese Patents JP 05339565 and JP 3229654 disclose indole derivatives for electroluminescent devices.

U.S. Pat. No. 5,342,547 discloses indole derivatives for controlling underwater fouling.

Whitehead and Whitesitt, *Journal of Medicinal Chemistry* (1974), 17(12), 1298-304 discloses the effects of lipohilic substituents on biological properties of indoles.

Co-pending International Patent Application PCT/US04/00017 discloses indole derivative agents as mineralocorticoid and glucocorticoid receptor modulators.

SUMMARY OF THE INVENTION

The present invention is directed to the discovery that certain indole-derivative compounds, as defined below, are modulators of steroid hormone nuclear receptors and, therefore, may have utility as pharmaceutical agents. Accordingly, the present invention provides a compound of the formula:

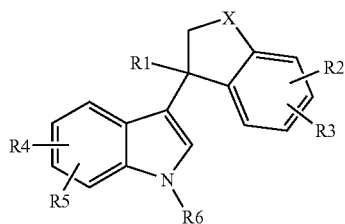

Formula I wherein,

X represents —$CH_2$—, —$CH_2CH_2$—, —$CH_2CH_2CH_2$—, —$CH_2O$—, —$CH_2S$—, or —$CH_2NR^{10}$—;

$R^1$ represents hydrogen, ($C_1$-$C_4$)alkyl, ($C_3$-$C_7$)cycloalkyl, hydroxy($C_1$-$C_4$)alkyl, halo($C_1$-$C_4$)alkyl, ($C_1$-$C_4$)alkyl-heterocycle, ($C_1$-$C_4$)alkyl-NH($C_1$-$C_4$)alkylamine, or ($C_1$-$C_4$)alkyl-N,N-($C_1$-$C_4$)dialkylamine;

$R^2$ represents hydrogen, halo, ($C_1$-$C_4$)alkyl, heterocycle, or substituted heterocycle;

$R^3$ represents hydrogen, halo, ($C_1$-$C_4$)alkyl, heterocycle, or substituted heterocycle;

$R^4$ represents hydrogen, halo, amino, nitro, ($C_1$-$C_4$)alkyl, ($C_1$-$C_4$)alkoxy, NH $SO_2R^7$, $NHCOR^8$, or $COR^9$;

$R^5$ represents hydrogen or halo;

$R^6$ represents hydrogen or ($C_1$-$C_4$)alkyl;

$R^7$ represents ($C_1$-$C_4$)alkyl, aryl, NH($C_1$-$C_4$)alkylamine, or N,N-($C_1$-$C_4$)dialkylamine;

$R^8$ represents ($C_1$-$C_4$)alkyl, ($C_1$-$C_4$)alkoxy, or aryl($C_1$-$C_4$)alkoxy; and $R^9$ represents ($C_1$-$C_4$)alkyl or ($C_1$-$C_4$)alkoxy;

$R^{10}$ represents hydrogen, ($C_1$-$C_4$)alkyl, ($C_3$-$C_7$)cycloalkyl, ($C_1$-$C_4$)alkyl-($C_3$-$C_7$)cycloalkyl;

or a pharmaceutically acceptable salt thereof.

As another aspect, the present invention provides a method of treating a physiological disorder susceptible to steroid hormone nuclear receptor modulation comprising administering to a patient in need thereof an effective amount of a compound of Formula I as described herein and above. Examples of such disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, atherosclerosis, Bartter's Syndrome, disorders associated with excess catecholamine levels, diastolic and systolic congestive heart failure (CHF), peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis; urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, cutaneous T-cell lymphoma, psychoses, cognitive disorders (such as memory disturbances), mood disorders (such as depression and bipolar disorder), anxiety disorders, and personality disorders.

As a further aspect, the present invention provides a method of treating a physiological disorder susceptible to mineralocorticoid or glucocorticoid receptor modulation comprising administering to a patient in need thereof an effective amount of a compound of Formula I as described herein and above. As a more particular aspect, the present invention provides a method of treating a physiological disorder susceptible to mineralocorticoid or glucocorticoid receptor antagonism comprising administering to a patient in need thereof an effective amount of a compound of Formula I. As an even more particular aspect the present invention provides a method of treating hypertension (isolated systolic and combined systolic/diastolic), systolic and/or diastolic congestive heart failure, atherosclerosis, rheumatoid arthritis or inflammation comprising administering to a patient in need thereof an effective amount of a compound of Formula I as described herein and above.

As a separate aspect, the present invention also provides a method of modulating a steroid hormone nuclear receptor comprising contacting said receptor with an effective amount of a compound of Formula I. More particularly, the present invention provides a method of modulating the mineralocorticoid or glucocorticoid receptor comprising contacting said receptor with an effective amount of a compound of Formula I. More particularly still, the present invention provides a method of antagonizing the mineralocorticoid or glucocorticoid receptor comprising contacting said receptor with an effective amount of a compound of Formula I, as described herein and above.

In addition, the present invention provides pharmaceutical compositions of compounds of Formula I, including any pharmaceutically acceptable salts and hydrates thereof, comprising a compound of Formula I in combination with a pharmaceutically acceptable carrier, diluent or excipient.

This invention also encompasses novel intermediates, and processes for the synthesis of the compounds of Formula I.

The present invention also provides the use of a compound of Formula I, or a pharmaceutically acceptable salt thereof, for the treatment of a physiological disorder susceptible to steroid hormone nuclear receptor modulation. More particularly, the present invention provides the use of a compound of Formula I, or a pharmaceutically acceptable salt thereof, for treating hypertension, congestive heart failure, atherosclerosis, rheumatoid arthritis or inflammation. Further still, the present invention also provides the use of a compound of Formula I, or a pharmaceutically acceptable salt thereof, for the manufacture of a medicament for treating a physiological disorder susceptible to steroid hormone nuclear-receptor modulation. More particularly, the present invention provides the use of a compound of Formula I, or a pharmaceutically acceptable salt thereof, for the manufacture of a medicament for treating hypertension, congestive heart failure, atherosclerosis, rheumatoid arthritis or inflammation.

DETAILED DESCRIPTION OF THE INVENTION

The present invention provides compounds of Formula I with affinity for steroid hormone nuclear receptors, particularly MR and/or GR, which could be used to modulate (i.e. repress, antagonize, agonize, partially antagonize, partially agonize) nuclear receptor activity and target gene expression, thereby influencing physiological functions related to steroid hormone levels and/or steroid hormone receptor activity. In this regard, compounds of Formula I are believed to be useful in treating or preventing a multitude of physiological disorders susceptible to steroid hormone nuclear receptor modulation. Thus, methods for the treatment or prevention of physiological disorders susceptible to steroid hormone nuclear receptor modulation constitute another important embodiment of the present invention. As a particular aspect, the present invention provides compounds useful as mineralocorticoid or glucocorticoid receptor modulators. As a more particular aspect, the present invention provides compounds useful as mineralocorticoid or glucocorticoid receptor antagonists.

As will be understood by the skilled artisan, some of the compounds useful for the methods of the present invention may be available for prodrug formulation. As used herein, the term "prodrug" refers to a compound of Formula I which has been structurally modified such that in vivo the prodrug is converted, for example, by hydrolytic, oxidative, reductive, or enzymatic cleavage, into the parent molecule ("drug") as given by Formula I, Such prodrugs may be, for example, metabolically labile ester derivatives of the parent compound where said parent molecule bears a carboxylic acid group. Conventional procedures for the selection and preparation of suitable prodrugs are well known to one of ordinary skill in the art.

It is also understood that many of the steroid hormone nuclear receptor modulators of the present invention may exist as pharmaceutically acceptable salts and, as such, pharmaceutically acceptable salts are therefore included within the scope of the present invention. The term "pharmaceutically acceptable salt" as used herein refers to salts of the compounds of Formula I, which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. It is further understood by the skilled reader that salt forms of pharmaceutical compounds are commonly used because they are often more readily crystallized, or more readily purified, than are the free bases. In all cases, the use of the pharmaceutical compounds of the present invention as salts is contemplated in the description herein. Hence, it is understood that where compounds of Formula I are capable of forming salts, the pharmaceutically acceptable salts and isoforms thereof are encompassed in the names provided herein.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenyl acetate, phenyl propionate; phenyl butyrate, citrate, lactate, α-hydroxybutyrate, glycolate, tartrate, methanesulfonate, propanesulfonate, naphthalene-1-sulfonate, napththalene-2-sulfonate, mandelate and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

As used herein, the term "stereoisomer" refers to a compound made up, of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. All such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond from the chiral carbon toward the lowest priority group. The term "S" (sinister) refers to that configuration of a chiral center with a counterclockwise relationship of group priorities (highest to second lowest) when viewed along the bond from the chiral carbon toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

In addition, as will be appreciated by one of ordinary skill in the art compounds of the present invention containing a carbon-carbon double bond may exist as geometric isomers. Two methods are commonly used to designate the specific isomers, the "cis-trans" method and the "E and Z" method, which methods designate a particular isomer based on whether the groups attached to each of the ethylene carbons are the same or different. A discussion of geometric isomerism and the naming of specific isomers is found in March, "Advanced Organic Chemistry", John Wiley & Sons, 1992, Chapter 4. All such geometric isomers, as well as mixtures of individual isomers, are contemplated and provided by the present invention.

As appreciated by one of ordinary skill in the art, suitable oxygen or nitrogen protecting groups are used as needed. Suitable oxygen or nitrogen protecting groups, as used herein, refers to those groups intended to protect or block the oxygen or nitrogen group against undesirable reactions during synthetic procedures. The suitability of the oxygen or nitrogen protecting group used will depend upon the conditions that will be employed in subsequent reaction steps wherein protection is required, and is well within the knowledge of one of ordinary skill in the art. Commonly used protecting groups suitable for practicing the present invention are disclosed in "Protective Groups in Organic Synthesis, 3rd Edition" by Theodara Greene, Peter G. M. Wuts, John Wiley & Sons, New York (1999).

As used herein the term "$(C_1-C_4)$alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "$(C_1-C_4)$alkyl" is included within the definition of "$(C_1-C_6)$alkyl".

As used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. It is understood that the terms "$(C_1-C_4)$alkyl" and "$(C_1-C_6)$alkyl" are included within the definition of "$(C_1-C_{10})$alkyl".

As used herein, the terms "Me", "Et", "Pr", "I—Pr", "Bu" and "t-Bu" refer to methyl, ethyl, propyl, isopropyl, butyl and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methoxy, ethoxy, n-propoxy, isopropoxy, n-butoxy, and the like. As used herein the term "$(C_1-C_6)$alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like. It is understood that the term "$(C_1-C_4)$alkoxy" is included within the definition of "$(C_1-C_6)$alkoxy".

As used herein, the term "hydroxy$(C_1-C_4)$alkyl" refers to a straight or branched, monovalent, saturated aliphatic chain of 1 to 4 carbon atoms bearing a hydroxyl group attached to one of the carbon atoms. As used herein, the term "hydroxy$(C_1-C_6)$alkyl" refers to a straight or branched, monovalent, saturated aliphatic chain of 1 to 6 carbon atoms bearing a hydroxyl group attached to one of the carbon atoms. It is understood that the term "hydroxy$(C_1-C_4)$alkyl" is included within the definition of "hydroxy$(C_1-C_6)$alkyl". As used herein, the term "hydroxy$(C_1-C_4)$alkoxy" refers to an oxygen atom bearing a straight or branched, monovalent, saturated aliphatic chain of 1 to 4 carbon atoms, further bearing a hydroxyl group attached to one of the carbon atoms. As used herein, the term "hydroxy$(C_1-C_6)$alkoxy" refers to an oxygen atom bearing a straight or branched, monovalent, saturated aliphatic chain of 1 to 6 carbon atoms, further bearing a hydroxyl group attached to one of the carbon atoms. It is understood that the term "hydroxy($C_1$-$C_4$)alkoxy" is included within the definition of "hydroxy($C_1$-$C_6$)alkoxy".

As used herein, the terms "halo", "halide" or "hal" of "Hal" refer to a chlorine, bromine, iodine or fluorine atom, unless otherwise specified herein.

As used herein, the term "halo($C_1$-$C_4$)alkyl" refers to a straight or branched, monovalent, saturated aliphatic chain of 1 to 4 carbon atoms bearing one or more halo groups attached to one or more of the carbon atoms. As used herein, the term "halo($C_1$-$C_6$)alkyl" refers to a straight or branched, monovalent, saturated aliphatic chain of 1 to 6 carbon atoms bearing one or more halo groups attached to one or more of the carbon atoms. It is understood that the term "halo($C_1$-$C_4$)alkyl" is included within the definition of "halo($C_1$-$C_6$)alkyl". As used herein, the term "halo($C_1$-$C_4$)alkoxy" refers to an oxygen atom bearing a straight or branched, monovalent, saturated aliphatic chain of 1 to 4 carbon atoms, further bearing one or more halo groups attached to one or more of the carbon atoms. As used herein, the term "halo($C_1$-$C_6$)alkoxy" refers to an oxygen atom bearing a straight or branched, monovalent, saturated aliphatic chain of 1 to 6 carbon atoms, further bearing one or more halo groups attached to one or more of the carbon atoms. It is understood that the term "halo($C_1$-$C_4$) alkoxy" is included within the definition of "halo($C_1$-$C_6$) alkoxy".

As used herein the term "($C_2$-$C_6$)alkenyl" refers to a straight or branched, monovalent, unsaturated aliphatic chain having from two to six carbon atoms and having a double bond. Typical ($C_2$-$C_6$)alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein the term "($C_2$-$C_6$)alkynyl" refers to a straight or branched, monovalent, unsaturated aliphatic chain having from two to six carbon atoms and having a triple bond. Typical ($C_2$-$C_6$)alkynyl groups include propynyl, ethynyl, and the like As used herein, the term "acyl" refers to a hydrogen or a ($C_1$-$C_6$)alkyl group attached to a carbonyl group. Typical acyl groups include formyl, acetyl, propionyl, butyryl, valeryl, and caproyl.

As used herein, the term "aryl" refers to a monovalent carbocyclic group containing one or more fused or non-fused phenyl rings and includes, for example, phenyl, 1-or 2-naphthyl, 1,2-dihydronaphthyl, 1,2,3,4-tetrahydronaphthyl, and the like.

The term "substituted aryl" refers to an aryl group optionally substituted with one to three moieties, preferably one or two, chosen from the group consisting of halo, amino, cyano, ($C_1$-$C_4$)alkyl, ($C_1$-$C_4$)alkoxy, —S—($C_1$-$C_4$)alkyl.

As used herein, the term "aryl($C_1$-$C_6$)alkoxy" (or "($C_1$-$C_6$) alkoxy-aryl") refers to an oxygen atom bearing a straight or branched, monovalent, saturated aliphatic chain of 1 to 6 carbon atoms wherein said aliphatic chain, in turn, bears an aryl group. Examples of "aryl($C_1$-$C_6$)alkoxy" include benzyloxy, phenyl ethoxy, and the like.

As used herein the term "($C_3$-$C_{10}$)cycloalkyl" refers to a saturated hydrocarbon ring structure composed of one or more fused or unfused rings containing from three to ten carbon atoms. Typical ($C_3$-$C_{10}$)cycloalkyl groups include cyclopropyl, cyclobutyl, cyclopentyl, cyclohexyl, cycloheptyl, cyclooctyl, adamantanyl, and the like. "($C_3$-$C_7$)cycloalkyl" refers to a saturated hydrocarbon ring structure composed of one or more fused or unfused rings containing from three to seven carbon atoms. It is understood that the definition of "($C_3$-$C_7$)cycloalkyl" is included within the definition of "($C_3$-$C_{10}$)cycloalkyl". The term "substituted ($C_3$-$C_7$)cycloalkyl" refers to a "($C_3$-$C_7$)cycloalkyl group optionally substituted with one or two moieties chosen from the group consisting of halogen, hydroxy, cyano, nitro, amino, ($C_1$-$C_6$)alkyl, ($C_1$-$C_6$)alkoxy, ($C_1$-$C_4$)alkyl-($C_3$-$C_{10}$)cycloalkyl, ($C_1$-$C_4$)alkyl-aryl, ($C_1$-$C_6$)alkoxycarbonyl, N,N ($C_1$-$C_6$)dialkylamine, NH($C_1$-$C_6$)alkylamine, ($C_1$-$C_4$)alkyl-N,N-$C_1$-$C_6$dialkylamine, difluoromethyl, difluoromethoxy, trifluoromethyl, and trifluoromethoxy.

As used herein, the term "($C_1$-$C_4$)alkyl-($C_3$-$C_7$)cycloalkyl" refers to a straight or branched, monovalent, saturated aliphatic chain of 1 to 4 carbon atoms which has a ($C_3$-$C_7$)cycloalkyl attached to the aliphatic chain. Included within the term "($C_1$-$C_4$)alkyl-($C_3$-$C_7$)cycloalkyl" are the following:

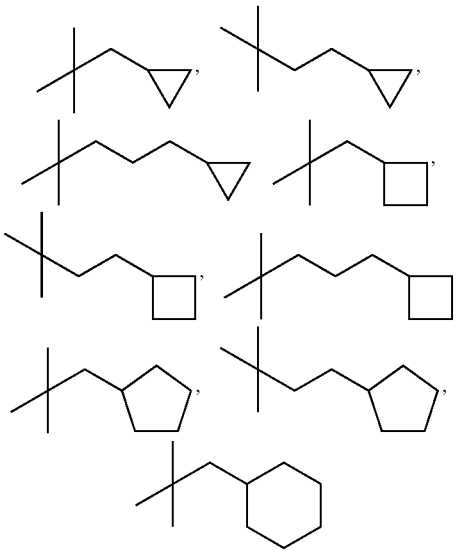

and the like. As used herein, the term "($C_1$-$C_4$)alkyl-substituted ($C_3$-$C_7$)cycloalkyl" refers to a straight or branched, monovalent, saturated aliphatic chain of 1 to 4 carbon atoms bearing an optionally substituted ($C_3$-$C_7$)cycloalkyl group attached to the aliphatic chain.

As used herein the term "heterocycle" refers to a saturated or unsaturated, five- or six-membered ring, which contains one to four heteroatoms selected from the group consisting of oxygen, sulfur, and nitrogen. It is understood that the remaining atoms are carbon and that the heterocycle may be attached at any point which provides for a stable structure. Examples of heterocycle groups include thiophenyl, furanyl, tetrahydrofuryl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl, and the like.

The term "substituted heterocycle" represents a heterocycle group optionally substituted with one or two moieties chosen from the group consisting of halo, amino, cyano, ($C_1$-$C_4$)alkyl, ($C_1$-$C_4$)alkoxy, —S—($C_1$-$C_4$)alkyl.

As used herein, the term "($C_1$-$C_4$)alkyl-heterocycle" refers to a straight or branched, monovalent, saturated aliphatic chain of 1 to 4 carbon atoms which has a heterocycle group attached to the aliphatic chain. Examples of "$(C_1-C_4)$alkyl-heterocycle" include:

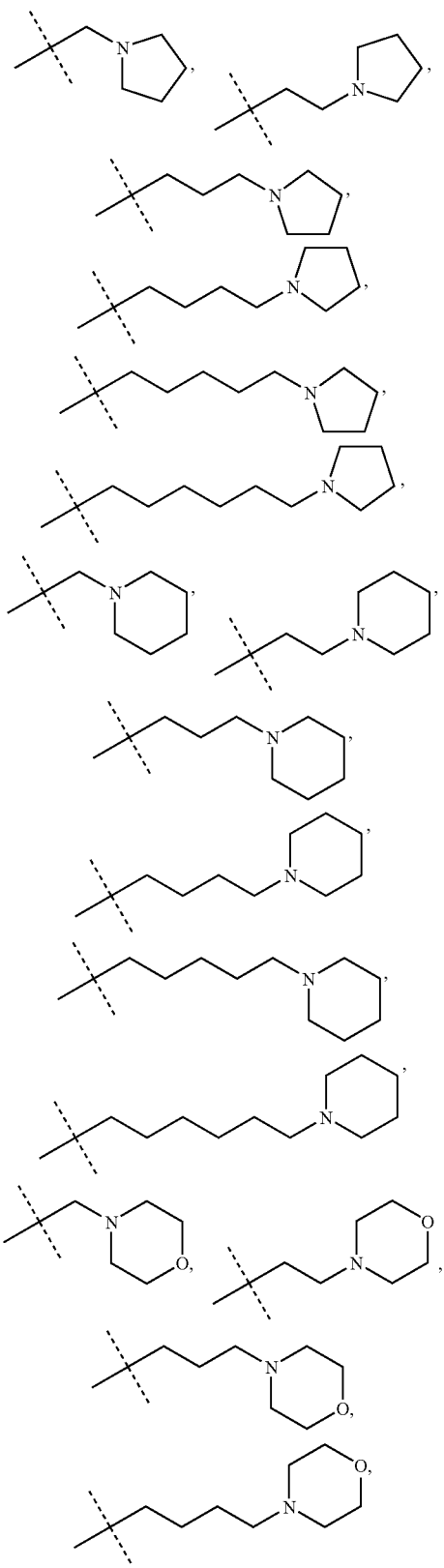

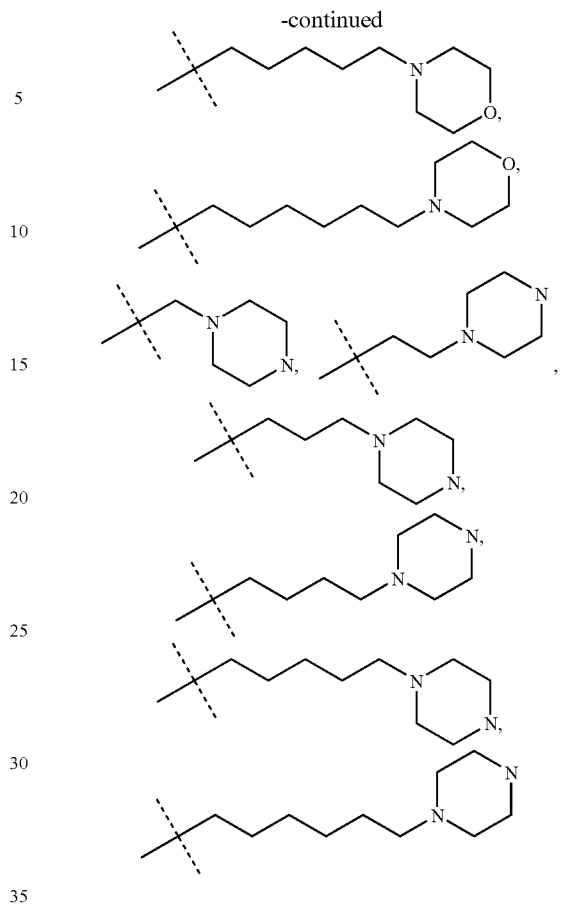

and the like.

The term "$(C_1-C_4)$alkyl-substituted heterocycle" refers to a straight or branched, monovalent, saturated aliphatic chain of 1 to 4 carbon atoms bearing an optionally substituted heterocycle group attached to the aliphatic chain.

As used herein, the term "NH—$(C_1-C_4)$ alkylamine" refers to a nitrogen atom substituted with a straight or branched, monovalent, saturated aliphatic chains of 1 to 4 carbon atoms. Included within the term "NH—$(C_1-C_4)$ alkylamine" are —NH(CH$_3$), —NH(CH$_2$CH$_3$), —NH(CH$_2$CH$_2$CH$_3$), —NH(CH$_2$CH$_2$CH$_2$CH$_3$), and the like.

As used herein the term "N,N-$(C_1-C_4)$dialkylamine" refers to a nitrogen atom substituted with two straight or branched, monovalent, saturated aliphatic chains of 1 to 4 carbon atoms. Included-within the term "N,N-$(C_1-C_4)$dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, —N,N(CH$_3$)(CH$_2$CH$_3$), —N,N(CH$_2$CH$_3$)(CH$_2$CH$_3$) and the like.

As used herein the term "$(C_1-C_4)$alkyl-N,N-$(C_1-C_4)$di-alkylamine" refers to straight. or branched, monovalent, saturated aliphatic chain of 1 to 4 carbon atoms which has an N,N-$(C_1-C_4)$dialkylamine attached to the aliphatic chain. Included within the term "$(C_1-C_4)$alkyl-N,N-$(C_1-C_4)$dialkylamine" are the following:

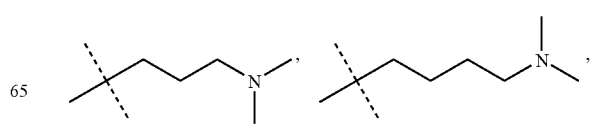

-continued

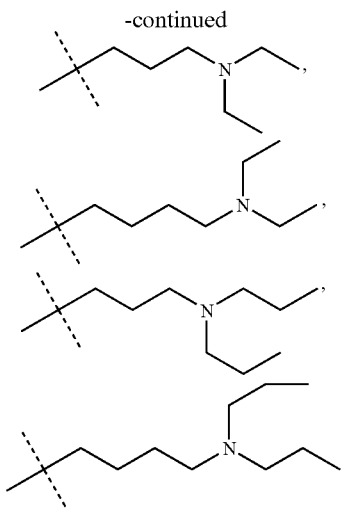

and the like.

As used herein the term "$(C_1-C_4)$alkyl-NH$(C_1-C_4)$alkylamine" refers to straight or branched, monovalent, saturated aliphatic chain of 1 to 4 carbon atoms which has an NH$(C_1-C_4)$alkylamine attached to the aliphatic chain. Included within the term "$(C_1-C_4)$alkyl-NH$(C_1-C_4)$alkylamine" are the following:

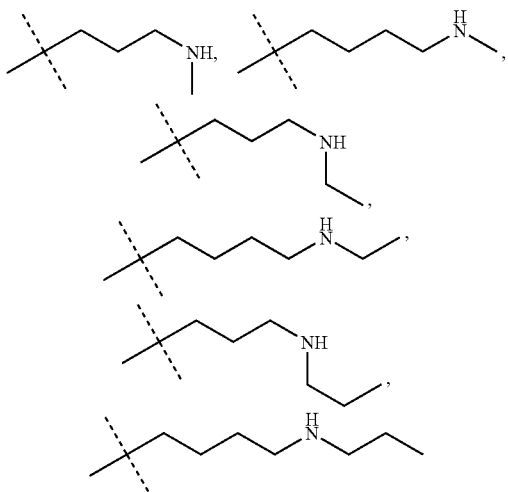

The designation "▬" refers to a bond that protrudes forward out of the plane of the page.

The designation "▥" refers to a bond that protrudes backward out of the plane of the page.

As used herein, the term "steroid hormone nuclear receptor modulator" refers to those nuclear hormone receptor ligands which bind to any one of GR, MR, AR, ER, or PR, of the larger class of nuclear hormone receptors, and either agonize, antagonize, partially agonize, or partially antagonize the receptor's activity.

As used herein the term "mineralocorticoid receptor" or "MR" refers to the mineralocorticoid receptor subtype, of the larger class of nuclear hormone receptors, which binds the mineralocorticoid hormone aldosterone, as its cognate ligand.

The term "mineralocorticoid receptor modulator" or "mineralocorticoid modulator" or "MR modulator" as used herein, refers to those nuclear hormone receptor ligands which bind to the mineralocorticoid receptor subtype and modulate (i.e. agonize, antagonize, partially agonize, or partially antagonize) the receptor activity. As a particular embodiment, the present invention provides antagonists of MR activity As used herein the term "glucocorticoid receptor" or "GR" refers to the glucocorticoid receptor subtype, of the larger class of nuclear hormone receptors, which binds the glucocorticoid hormones cortisol, corticosterone, or cortisone as its cognate ligand. The term "glucocorticoid receptor modulator" or "glucocorticoid modulator" or "GR modulator", as used herein, refers to those nuclear hormone receptor ligands which bind to the glucocorticoid receptor subtype and modulate (i.e. agonize, antagonize, partially agonize, or partially antagonize) the receptor activity.

As used herein, the term "disorder susceptible to steroid hormone nuclear receptor modulation" refers to any physiological disorder, of any origin, known or believed to be responsive to administration of a modulator (i.e. agonist, antagonist, partial agonist, or partial antagonist) of a steroid hormone nuclear receptor. Such disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, atherosclerosis, Bartter's Syndrome, disorders associated with excess catecholamine levels, diastolic and systolic congestive heart failure (CHF), peripheral vascular disease, atherosclerosis, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, BPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, cutaneous T-cell lymphoma, psychoses, cognitive disorders (such as memory disturbances), mood disorders (such as depression and bipolar disorder), anxiety disorders, and personality disorders.

As used herein the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human. As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as a mineralocorticoid receptor modulator. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the steroid hormone nuclear receptor modulator is administered as a combination of compounds, one of the compounds may be administered by one route, such as oral, and the other may be administered by the transdermal, percutaneous, pulmonary, intravenous, intramuscular, intranasal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, as described herein and above, including the pharmaceutically acceptable salts and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures. The following discussion provides typical procedures for preparing pharmaceutical compositions incorporating the compounds of the present invention. However, the following is in no way intended to limit the scope of the pharmaceutical compositions provided by the present invention.

Compositions are preferably formulated in a unit dosage form, each dosage containing, from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible. powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and 'the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It is understood by one of ordinary skill in the art that the procedures as described above can also be readily applied to a method of treating physiological disorders susceptible to steroid hormone nuclear receptor modulation, and particularly congestive heart failure.

Particular Aspects of the Compounds and Methods of the Invention

The following list sets out several groupings of particular substituents for compounds of Formula I. It will be understood that compounds of Formula I having such particular substituents, and the methods employing such compounds, represent particular aspects of the present invention. It will be further understood that each of these groupings of particular substituents may be combined with other provided groupings, to create still additional particular aspects of the compounds of the present invention Therefore, a particular aspect of the present invention is one wherein the compound of Formula I, is one wherein:

(a) X represents —$CH_2$—, —$CH_2CH_2$—, —$CH_2CH_2CH_2$—, —$CH_2O$—, or —$CH_2S$—;
(b) X represents —$CH_2$—, —$CH_2CH_2$—, or —$CH_2O$—;
(c) X represents —$CH_2$—;
(d) X represents —$CH_2CH_2$—;
(e) X represents —$CH_2O$—; or
(f) X represents —$CH_2NR^{10}$—.
(g) $R^1$ represents hydrogen, ($C_1$-$C_4$)alkyl, ($C_3$-$C_7$)cycloalkyl, hydroxy($C_1$-$C_4$)alkyl, halo($C_1$-$C_4$)alkyl, ($C_1$-$C_4$)alkyl-heterocycle, ($C_1$-$C_4$)alkyl-NH($C_1$-$C_4$)alkylamine, or ($C_1$-$C_4$)alkyl-N,N-($C_1$-$C_4$)dialkylamine;
(h) $R^1$ represents hydrogen, methyl, ethyl, propyl, isopropyl, ($C_3$-$C_7$)cycloalkyl, hydroxy($C_1$-$C_4$)alkyl, halo($C_1$-$C_4$)alkyl, ($C_1$-$C_4$)alkyl-heterocycle, ($C_1$-$C_4$)alkyl-NH($C_1$-$C_4$)alkylamine, or ($C_1$-$C_4$)alkyl-N,N-($C_1$-$C_4$)dialkylamine;
(i) $R^1$ represents hydrogen, methyl, ethyl, propyl, or isopropyl;
(j) $R^1$ represents hydrogen, methyl or ethyl;
(k) $R^1$ represents methyl or ethyl;
(l) $R^1$ represents hydrogen or ($C_3$-$C_7$)cycloalkyl;
(m) $R^1$ represents ($C_3$-$C_7$)cycloalkyl;
(n) $R^1$ represents cyclopropyl;
(o) $R^1$ represents hydrogen or hydroxy($C_1$-$C_4$)alkyl;
(p) $R^1$ represents hydroxy($C_1$-$C_4$)alkyl;
(q) $R^1$ represents 3-hydroxypropyl;
(r) $R^1$ represents hydrogen or ($C_1$-$C_4$)alkyl-heterocycle;
(s) $R^1$ represents ($C_1$-$C_4$)alkyl-heterocycle;
(t) $R^1$ represents 3-morpholino-4-yl propyl
(u) $R^1$ represents hydrogen or halo($C_1$-$C_4$)alkyl;
(v) $R^1$ represents halo($C_1$-$C_4$)alkyl;
(w) $R^1$ represents 3-iodopropyl;
(x) $R^1$ represents hydrogen or ($C_1$-$C_4$)alkyl-NH($C_1$-$C_4$)alkylamine;
(y) $R^1$ represents ($C_1$-$C_4$)alkyl-NH($C_1$-$C_4$)alkylamine;
(z) $R^1$ represents 3-methylamino propyl
(aa) $R^1$ represents hydrogen or ($C_1$-$C_4$)alkyl-N,N-($C_1$-$C_4$)dialkylamine;
(bb) $R^1$ represents ($C_1$-$C_4$)alkyl-N,N-($C_1$-$C_4$)dialkylamine; or
(cc) $R^1$ represents 3-dimethylamino propyl.
(dd) $R^2$ represents hydrogen, halo, methyl, ethyl, propyl, isopropyl, heterocycle, or substituted heterocycle;.
(ee) $R^2$ represents hydrogen, fluoro, chloro, bromo, methyl, ethyl, propyl, isopropyl, or heterocycle;
(ff) $R^2$ represents hydrogen, fluoro, chloro, or bromo;
(gg) $R^2$ represents hydrogen or fluoro;
(hh) $R^2$ represents fluoro;

(ii) $R^2$ represents hydrogen, methyl, ethyl, propyl, or isopropyl;
(jj) $R^2$ represents hydrogen or heterocycle;
(kk) $R^2$ represents pyrrazolyl; or
(ll) $R^2$ represents hydrogen;
(mm) $R^3$ represents hydrogen, fluoro, chloro, or bromo;
(nn) $R^3$ represents hydrogen, fluoro, or chloro;
(oo) $R^3$ represents hydrogen or fluoro;
(pp) $R^3$ represents fluoro; or
(qq) $R^3$ represents hydrogen;
(rr) $R^4$ represents hydrogen, halo, amino, nitro, $(C_1-C_4)$alkyl, $(C_1-C_4)$alkoxy, $NH\ SO_2R^7$, $NHCOR^8$ wherein R8 represents $(C_1-C_4)$alkyl or $(C_1-C_4)$alkoxy, or $COR^9$ wherein R9 represents $(C_1-C_4)$alkyl or $(C_1-C_4)$alkoxy;
(ss) $R^4$ represents hydrogen, halo, amino, nitro, $(C_1-C_4)$alkyl, $(C_1-C_4)$alkoxy, $NH\ SO_2R^7$, $NHCOR^8$ wherein R8 represents methyl, ethyl, methoxy, or ethoxy, or $COR^9$ wherein R9 represents methyl, ethyl, methoxy, or ethoxy;
(tt) $R^4$ represents hydrogen, halo, amino, nitro, $(C_1-C_4)$alkyl, $(C_1-C_4)$alkoxy, $NH\ SO_2R^7$, $NHCOR^8$ wherein R8 represents methyl or methoxy, or $COR^9$ wherein R9 represents methyl or methoxy;
(uu) $R^4$ represents hydrogen, halo, amino, nitro, $(C_1-C_4)$alkyl, $(C_1-C_4)$alkoxy, or $NH\ SO_2R^7$;
(vv) $R^4$ represents hydrogen, fluoro, chloro, bromo, amino, nitro, methyl, ethyl, methoxy, ethoxy or $NH\ SO_2R^7$;
(ww) $R^4$ represents hydrogen, fluoro, chloro, bromo, amino, or nitro;
(xx) $R^4$ represents fluoro, chloro, bromo, amino, or nitro;
(yy) $R^4$ represents fluoro, chloro, or bromo;
(zz) $R^4$ represents amino or nitro;
(aaa) $R^4$ represents hydrogen, methyl, ethyl, methoxy, or ethoxy;
(bbb) $R^4$ represents methyl, ethyl, methoxy, or ethoxy;
(ccc) $R^4$ represents methyl or ethyl;
(ddd) $R^4$ represents methoxy or ethoxy;
(eee) $R^4$ represents hydrogen or $NH\ SO_2R^7$;
(fff) $R^4$ represents hydrogen or $NH\ SO_2R^7$ wherein R7 represents $(C_1-C_4)$alkyl, aryl, or $N,N-(C_1-C_4)$dialkylamine;
(ggg) $R^4$ represents hydrogen, $NHSO_2CH_3$, $NHSO_2CH_2CH_3$, $NHSO_2(C_6H_5)$, or $NHSO_2N(CH_3)_2$;
(hhh) $R^4$ represents $NHSO_2CH_3$, or $NHSO_2CH_2CH_3$;
(iii) $R^4$ represents $NHSO_2CH_3$; or
(jjj) $R^4$ represents hydrogen.
(kkk) $R^5$ represents hydrogen, fluoro, or chloro;
(lll) $R^5$ represents hydrogen.
(mmm) $R^6$ represents hydrogen, methyl, or ethyl;

In addition, as yet another particular embodiment of the present invention, the compounds of Formula I have the following configuration

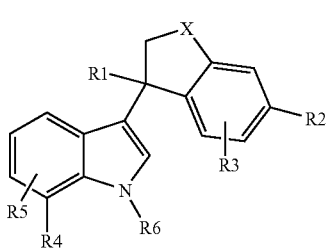

Formula I

In addition, it will be understood that where X represents $-CH_2O-$, $-CH_2S-$, or $-CH_2NR^{10}$, either one of the heteroatom or the carbon of such groups maybe directly attached to the fused phenyl ring.

Compounds of Formula I can be chemically prepared, for example, by following the synthetic routes set forth in the Schemes below. However, the following. discussion is not intended to be limiting to the scope of the present invention in any way. For example, the specific synthetic steps for the routes described herein may be combined in different ways, or with steps from different schemes, to prepare additional compounds of Formula I. Further, it should be recognized that the sequence in which the synthetic reactions take place is not implied and can be done in any fashion to achieve the desired final product. All substituents, unless otherwise indicated, are as previously defined. The reagents and starting materials are readily available to one of ordinary skill in the art. Other necessary reagents and starting materials may be made by procedures which are selected from standard techniques of organic and heterocyclic chemistry, techniques which are analogous to the syntheses of known structurally similar compounds, and the procedures described in the Preparations and Examples below, including any novel procedures. In addition, one of ordinary skill will appreciate that many of the necessary reagents or starting materials can be readily obtained from commercial suppliers.

Compounds of Formula I can be synthesized by coupling the appropriately substituted or unsubstituted indole with the appropriately substituted or unsubstituted carbinol according to procedures as generally described in Scheme I, below. Any subsequent modifications deemed necessary to produce the final product of Formula I, including but not limited to deprotection reactions, can be readily performed by one of ordinary skill in the art. The appropriately substituted or unsubstituted carbinols used in the following procedures can either be purchased from commercial vendors or can be prepared from appropriately substituted or unsubstituted ketones, as depicted in Scheme I, using methods known in the art. The ketones for use in the following procedures are either purchased from commercial suppliers, or synthesized as described in Schemes II through VIII below. The indoles for use in the following procedures are also either purchased from commercial suppliers, or synthesized in the manner as described in Schemes IX and X.

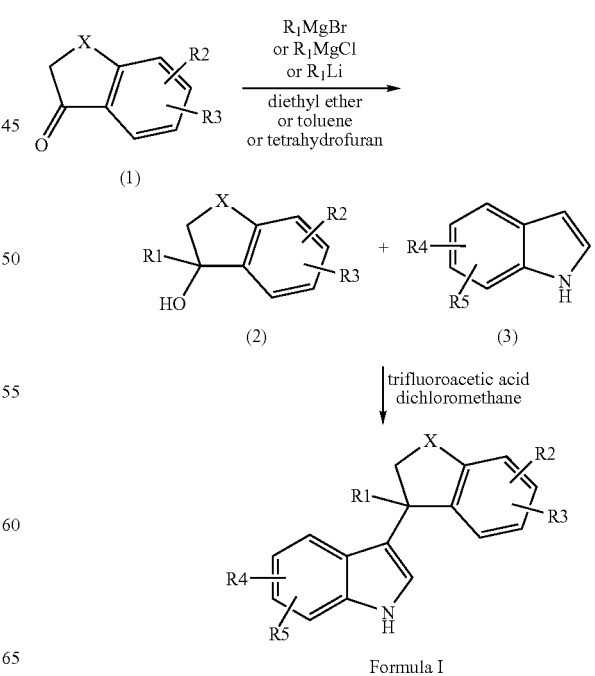

In Scheme I, an appropriately substituted or unsubstituted ketone of the general structure (1) is dissolved in a suitable solvent such as diethyl ether or toluene or tetrahydrofuran. An alkyl magnesium halide or alkyl lithium reagent is then added under nitrogen at room temperature or lower temperatures and the reaction mixture is allowed to proceed from ten minutes to several days. The reaction is then quenched using a suitable reagent such as aqueous ammonium chloride and the carbinol of general structure (2) is isolated using techniques common in the art. The electrophilic aromatic substitution occurs by methods known in the art. For example, the appropriately substituted or unsubstituted indole (3), and the appropriately substituted or unsubstituted carbinol (2) are first dissolved in a suitable solvent such as dichloromethane or acetic acid or methanol then treated with a suitable protic or Lewis' acid such as trifluoroacetic acid, boron trifluoride etherate, hydrogen chloride or aluminum chloride. The reaction proceeds in anywhere from ten minutes to several days depending on the stability of the starting materials. The product of Formula I can then be isolated by normal phase chromatographic methods or recrystallization techniques commonly employed in the art.

Substituted or unsubstituted indanones of the general structure (6) where $R^2$ and $R^3$ independently can be, for example, hydrogen, alkyl, aryl, halo or heterocycle can be synthesized according to Scheme II using common techniques in the art.

SCHEME II

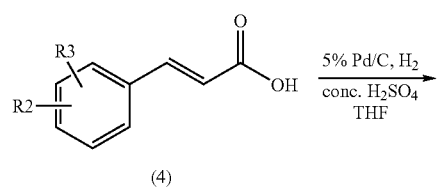

(4)

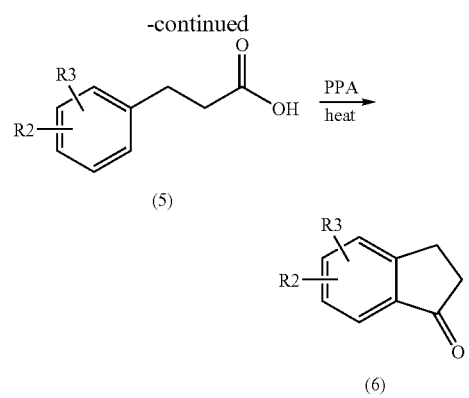

In Scheme II, an appropriately substituted or unsubstituted cinnamic acid of the general structure (4) is reduced using methods known in the art. The hydrogenation can occur in a suitable solvent such as tetrahydrofuran or acetic acid employing, but not limited to, an appropriate catalyst such as palladium on carbon or palladium hydroxide or platinum oxide. The reaction takes place under an atmosphere of hydrogen at various pressures and temperatures. Addition of acid such as concentrated sulfuric acid may facilitate the reaction. The substituted or unsubstituted 3-aryl propionic acid of the general structure (5) can then be cyclized using methods common in the art such as heating the reduced substituted or unsubstituted cinnamic acid with polyphosphoric acid at various temperatures with or without a suitable solvent (Scheme II) to form substituted or unsubstituted indanones of the general structure (6). Alternatively, (5) can be activated by conversion to the corresponding acid halide or anhydride using a suitable reagent such as thionyl chloride or trifluoroacetic anhydride and then cyclized in the presence of a suitable Lewis acid such as aluminum trichloride or boron trifluoride etherate in an appropriate solvent using techniques and methods common in the alt.

Substituted or unsubstituted tetralones of the general structure (12) where $R^2$ and $R^3$ independently can be, for example, hydrogen, alkyl, aryl, halo or heterocycle can be synthesized according to Scheme III using common techniques in the art.

SCHEME III

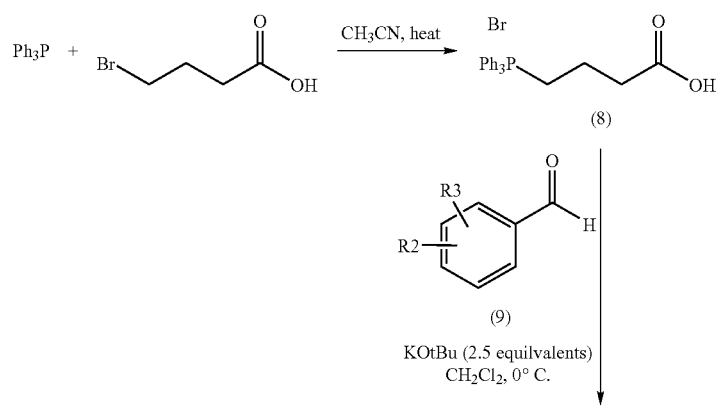

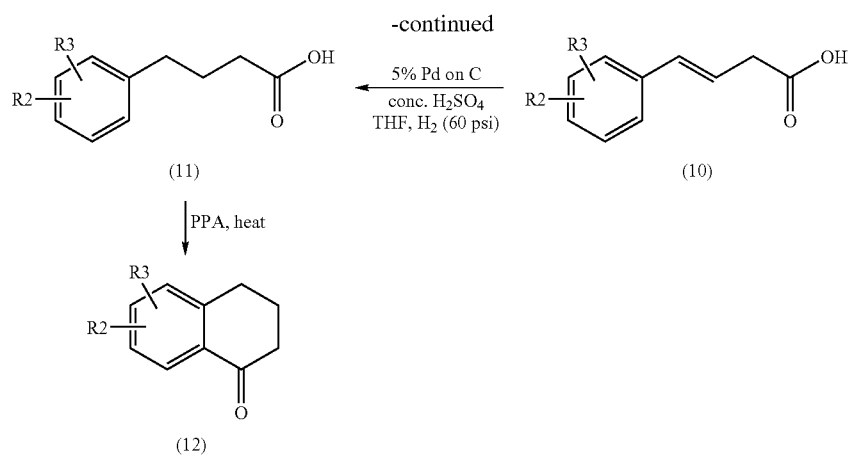

(11)　(10)

(12)

In Scheme III, triphenylphosphine can be reacted with 4-bromobutanoic acid in a suitable solvent such as acetonitrile at various temperatures to obtain the Wittig reagent (2-carboxy-ethyl)-triphenyl-phosphonium bromide (8). As in Scheme III, (2-carboxy-ethyl)-triphenyl-phosphonium bromide (8) can be used with an appropriately substituted or unsubstituted aldehyde on the general structure (9) in the presence of a suitable base such as potassium t-butoxide or sodium hydride and in a suitable solvent such as dichloromethane or tetrahydrofuran at various temperatures to obtain the corresponding substituted or unsubstituted beta-gamma-butenoic acid (10) using techniques common in the art. The isolated beta-gamma-butenoic acid (10) can be a mixture of cis/trans isomers depending on the substitution of the aryl ring, the base, the solvent, and other reaction conditions such as temperature and concentration of reagents. The substituted or unsubstituted beta-gamma-butenoic acid can be used in the next step as a cis/trans mixture or after chromatographic separation. The substituted or unsubstituted beta-gamma-butenoic acid can then be hydrogenated to a 4-aryl butenoic acid of general structure (11) and cyclized using the same or similar methods and conditions known in the art that were described in Scheme II above to obtain the substituted or unsubstituted tetralone of general structure (12).

Substituted or unsubstituted 4-chromanones of the general structure (16) where $R^2$ and $R^3$ independently can be, for example, hydrogen, alkyl, aryl, halo or heterocycle can be synthesized according to Scheme IV using common techniques in the art.

SCHEME IV

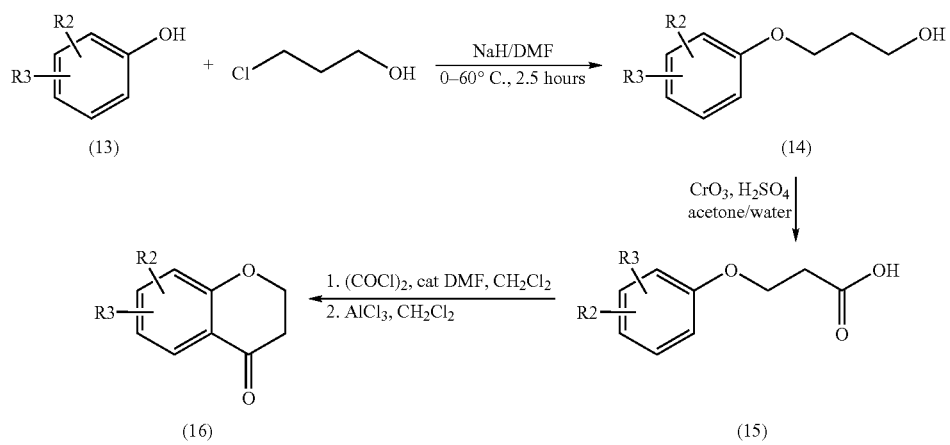

In Scheme IV, an appropriately substituted or unsubstituted phenol is alkylated with 3-chloro-1-propanol using a suitable base such as sodium hydride in a suitable solvent such as dimethylformamide. The resulting alcohol of general structure (14) can be isolated using standard methods known in the art. The alcohol moiety of (14) can be oxidized using standard oxidation procedures common in the art such as chromium trioxide in aqueous sulfuric acid/acetone. The resulting acid of general structure (15) can be converted to the corresponding acid halide using methods known in the art such as oxalyl chloride in dichloromethane with a catalytic amount of dimethylformamide; Intramolecular acylation of the aryl ring in (15) can be achieved using a suitable Lewis acid such as aluminum trichloride to obtain the corresponding chromanone of general structure (16).

Compounds of Formula I wherein $R^4$ represents amino or an amine derivative substituent such as $NHSO_2R^7$ or $NHCOR^8$ (as depicted by structures (18) and (19) below) can be prepared according to Scheme V using methods known in the art.

SCHEME V

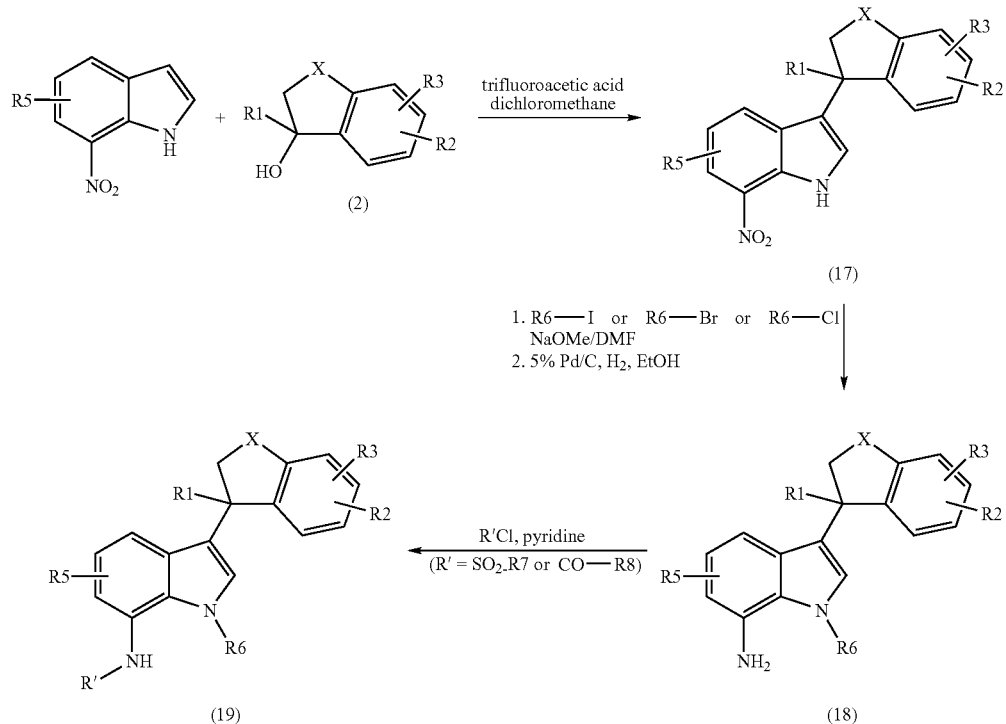

As depicted in Scheme V, a 7-nitroindole derivative can be condensed with a carbinol of the general structure (2) using conditions known to the art that were described in Scheme I above. Alkylation/acylation/sulphonylation of the indole nitrogen atom can take place in the presence of an appropriate alkylating/acylating/sulphonylating agent respectively such as methyl iodide, acetyl chloride, or methanesulphonyl chloride. A suitable base such as sodium methoxide or sodium hydride and solvent such as dimethylformamide must also be used. The alkylated/acylated/sulphonylated product can be isolated using standard techniques common in the art, such as aqueous workup, and chromatographic purification. Reduction of the nitro group can be achieved using methods known in the art. The nitro compound can be dissolved in an appropriate solvent such as ethyl acetate, methanol, ethanol, tetrahydrofuran, or acetic acid, then an appropriate catalyst is added such as palladium on carbon, or Pearlman's catalyst, or platinum oxide, and the resulting mixture is hydrogenated for 10 minutes to 6 hours. Products of the general structure (18) can be isolated using common techniques. The aniline nitrogen atom can then be alkylated/acylated/sulphonylated using an appropriate alkylating/acylating/sulphonylating agent and a suitable solvent/base such as pyridine. Co-solvents such as tetrahydrofuran, dimethyl sulfoxide, or dimethylformamide may also be added.

Further procedures for the synthesis of compounds of Formula I wherein $R^4$ represents amino or an amine derivative are provided by Scheme VI.

SCHEME VI

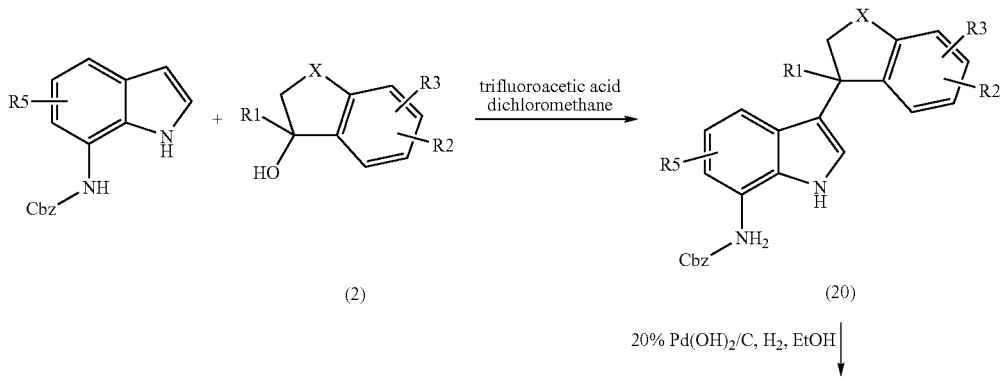

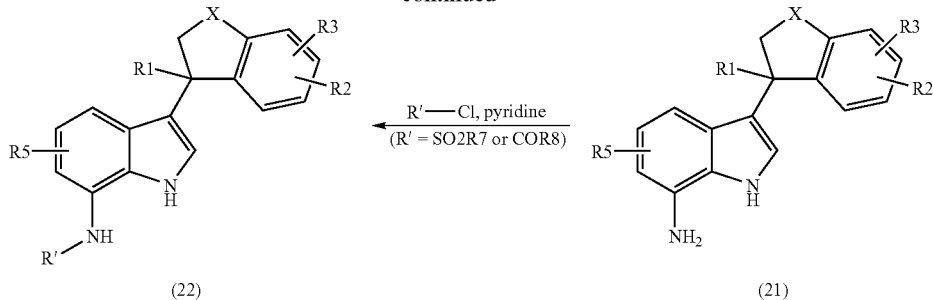

In Scheme VI, a Cbz-protected 7-aminoindole derivative (made according to procedures as described in Scheme X, below) can be condensed with a carbinol of the general structure (2) using conditions known to the art that were described in Scheme I above. Removal of the Cbz protecting group in structure (20) can be achieved using methods known in the art. Compound (20) can be dissolved in an appropriate solvent such as ethyl acetate, methanol, ethanol, tetrahydrofuran, or acetic acid, then an appropriate catalyst is added such as palladium on carbon, or Pearlman's catalyst, or platinum oxide, and the resulting mixture is hydrogenated using conditions known in the art. Products of the general structure (21) can be isolated using common techniques. The aniline nitrogen atom can then be alkylated/acylated/sulphonylated using an appropriate alkylating/acylating/sulphonylating agent such as methanesulphonyl chloride or acetyl chloride and a suitable solvent/base such as pyridine. Co-solvents such as tetrahydrofuran, dimethyl sulfoxide, or dimethylformamide may also be added.

Ketones of the general structure (24) can be prepared according to Scheme VII using methods known in the art. In Scheme VII, $R^X$ and $R^Y$ can independently be, for example, hydrogen, alkyl or acyl groups or part of a heterocyclic ring. such as imidazole, pyrrazole, pyrrole, or morpholine, and the like.

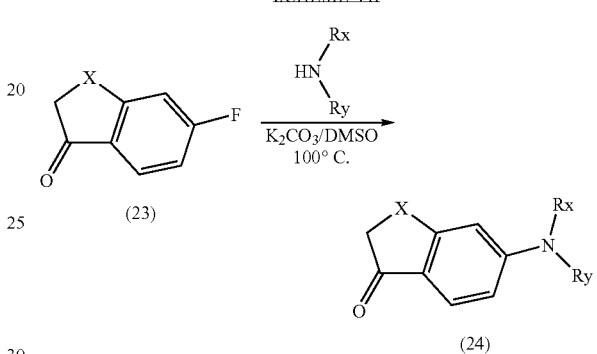

In Scheme VII, a ketone of structure (24) can be prepared by reacting a compound of structure (23) in an appropriate solvent such as dimethyl sulfoxide in the presence of a base such as potassium carbonate and a nucleophilic amine or nitrogen containing heterocycle. The reaction takes place at temperatures of 100 degrees Celcius to 300 degrees Celcius depending on the nucleophilicity of the nitrogen atom.

Compounds of Formula I wherein R1 is, for example, an alkyl-alkylamine derivative (as depicted by structure (29), below) can be prepared according to the reaction sequence in Scheme VIII. In Scheme VIII, $R^X$ and $R^Y$ can independently be, for example, hydrogen, alkyl or acyl groups or part of a heterocyclic ring such as imidazole, pyrrazole, pyrrole, or morpholine, and the like.

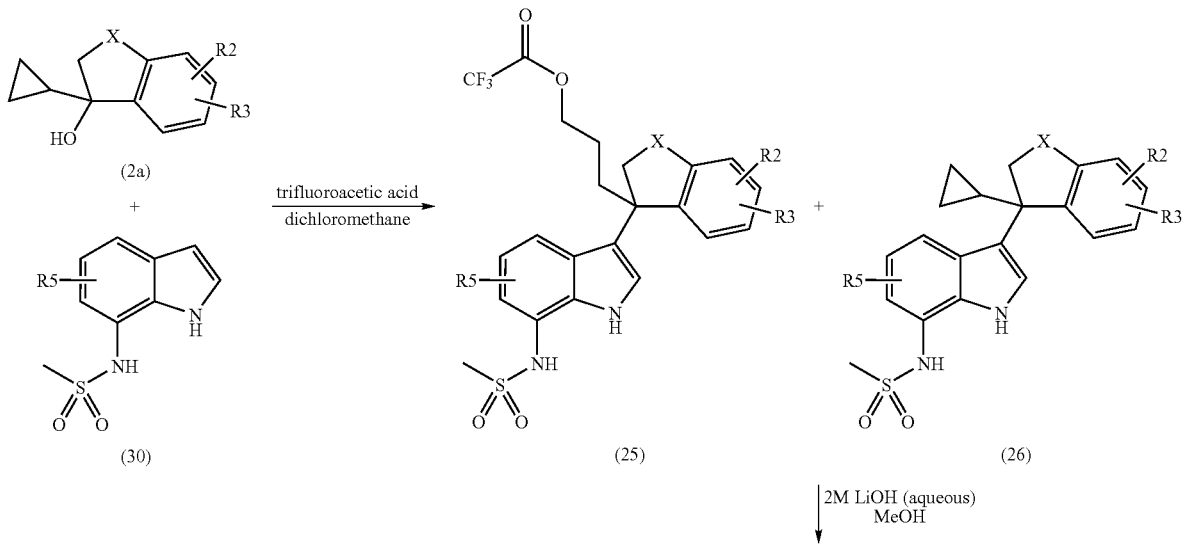

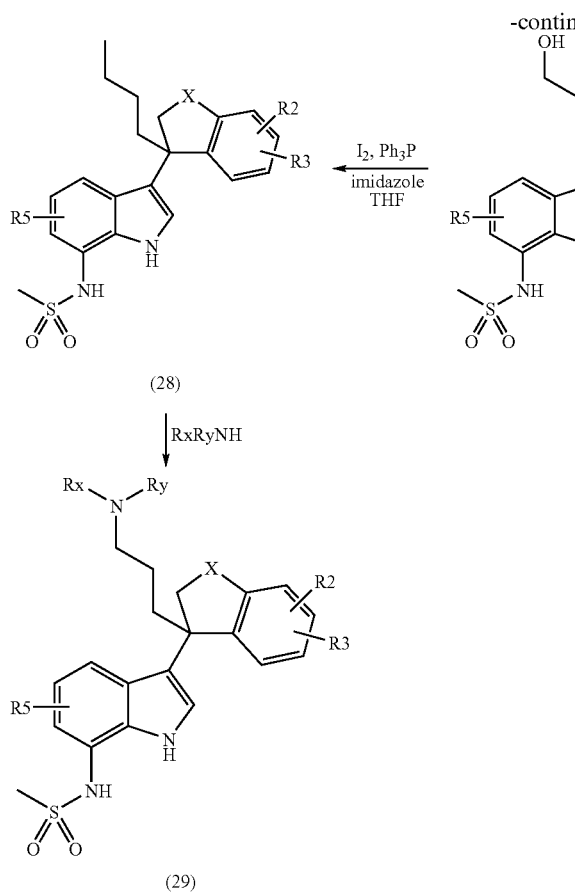

In Scheme VIII, the cyclopropyl carbinol of structure (2a) is condensed with a N-(1H-Indol-7-yl)-methanesulfonamide derivative (made according to procedures as described in Scheme IX, below) under the standard conditions that were described previously (Scheme I). A mixture of trifluoroacetate propyl ester (25) and product (26) results. Compounds (25) and (26) may be separated using standard techniques such as normal or reverse-phase chromatography or carried forward to the next step as a mixture. Hydrolysis of the TFA ester can take place in a suitable solvent such as methanol using an appropriate base such as aqueous lithium hydroxide. Isolation and separation of (27) from (26) can be achieved using standard techniques common in the art. The propyl alcohol (27) can be converted to the corresponding propyl halide (28) using standard Mitsunobu-type conditions. For example, an appropriate halogen such as iodine or bromine can be added to a mixture of triphenylphosphine and imidazole in tetrahydrofuran under nitrogen to prepare the Mitsunobu reagent. The alcohol (27) is then added as a solid or in solution in tetrahydrofuran and the reaction mixture is stirred until completion. The propyl iodide derivative can be isolated and purified using standard techniques such as aqueous workup and normal phase chromatography. The iodide derivative (28) can then be converted to a secondary or tertiary amine by reacting it with an excess of amine such as morpholine or dimethylamine. The reaction can be run either using the amine as the solvent or using an appropriate co-solvent such as tetrahydrofuran. Amines of the general structure (29) can then be isolated using methods common in the art.

Scheme IX depicts the preparation of N-(1H-Indol-7-yl)-methanesulfonamide derivatives using methods common in the art.

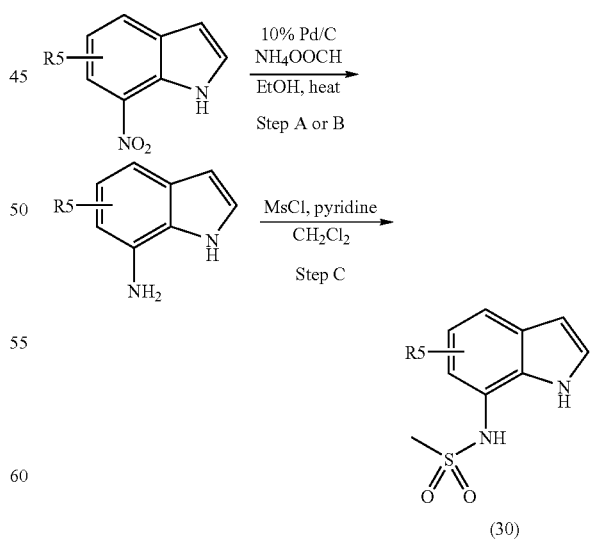

In Scheme IX, Step A or B, the nitro reduction occurs by methods commonly employed in the art. For example, a 7-nitroindole derivative (Step A) is dissolved in a suitable solvent such as ethanol, and is reduced by hydrogenation conditions, such as Pd/C and a hydrogen source like hydrogen gas or ammonium formate. The reaction may occur at room temperature to refluxing conditions and the product may be isolated by standard techniques such as filtration or standard aqueous workup. Alternatively, (Step B), the 7-nitroindole derivative is treated with a reducing agent, such as tin chloride dihydrate, at elevated temperatures. The reaction may proceed for about 1-24 hours. The product may be isolated by methods known in the art, such as a standard aqueous workup, and be purified via chromatography. In Scheme IX, Step C, the 7-aminoindole derivative is dissolved in dichloromethane and pyridine, and methanesulfonyl chloride is added. The reaction is stirred at room temperature for a minimum of six hours. The product of structure (30) may be isolated by methods known in the art, such as a standard aqueous workup, and may be purified via standard chromatography techniques.

In Scheme X, a 7-aminoindole derivative is protected with a Cbz group using conditions common in the art. For example, 7-aminoindole is dissolved in dichloromethane, aqueous sodium hydroxide is added, followed by Cbz chloride. After completion of the reaction, the Cbz-protected product (30) is isolated using techniques known in the art.

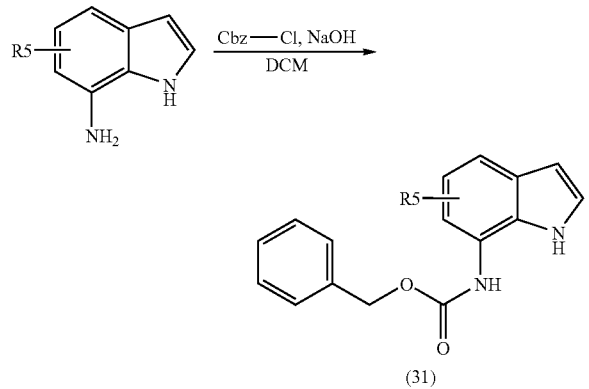

Determination of Biological Activity:

To demonstrate that compounds of the present invention have affinity for steroid hormone nuclear receptors, and thus have the capacity to modulate steroid hormone nuclear receptors, soluble MR and GR binding assays are performed. All ligands, radioligands, solvents, and reagents employed in the binding assays are readily available from commercial sources, or can be readily synthesized by the ordinarily skilled artisan.

Mineralocorticoid Receptor Binding Assay (Method 1):

The full length human MR gene is cloned from a human kidney or human brain cDNA library. Briefly, using synthetic oligonucleotide primers (Eli Lilly and Company, Indianapolis) directed to nucleotides 20-54 and 3700-3666 of the human MR, polymerase chain reaction (PCR) is performed under standard conditions using a human cDNA library. The PCR reaction is performed in a final volume of 50 µl containing about 1 µl of a 50× stock solution of polymerase; about 1 µl of a 50× stock solution of dNTP; about 5 µl of an appropriate PCR buffer; about 1 µl of each primer; about 5 µl of a H. kidney or H. brain cDNA library; and about 36 µl of water. The reaction is allowed to denature for about 30 seconds at 95 degrees Celsius, anneal for about 30 seconds at 55 degrees Celsius, and extend for about 5 minutes at 72 degrees Celsius, the sequence being repeated for a total of about 35 cycles. The desired PCR product (3.68 Kb) is confirmed by gel electrophoresis and subsequently cut from the gel and stored at about −20 degrees Celsius until extraction. To extract the cDNA product from the agarose gel, the QIAEX II Gel Extraction protocol (QIAGEN, Inc.) is employed according to the manufacturer's instructions. Following extraction, the MR cDNA is cloned into an appropriate cloning vector (Zero Blunt TOPO PCR Cloning Kit (Invitrogen, Inc.) and a pAcHLT-baculovirus transfer vector (B.D./Pharmingen), then expressed in SF9 insect cells, essentially according to manufacturer's instructions. Sf9 cells are grown at a scale where gram quantity cell pellets are obtained for subsequent use in the MR binding assay. Harvested cell pellets are lysed by repeated freeze-thaw cycles (about 4) in a suitable lysis buffer then centrifuged at about $1 \times 10^3$ G (with the supernatant being saved for future assays).

MR binding assays are performed in a final total volume of about 250 µl containing about 20-25 µg of protein and 0.5 nM of [$^3$H]-aldosterone plus varying concentrations of test compound or vehicle. The assay binding buffer consists of 30 mM sodium molybdate, 30 mM of TRIS-HCl, 5 mM sodium phosphate, 5 mM sodium pyrophosphate, and about 10% glycerol, pH=7.5.

Briefly, assays are prepared at RT in 96-well Falcon 3072 plates, each well containing 210 µl of binding buffer, 10 µl of [$^3$H]-aldosterone, 10 µl of test compound/vehicle, and 20 µl of the resuspended receptor protein extract. Incubations are carried out at 4 degrees Celsius with shaking for about 16 hours. 200 µl aliquots of each incubation are filtered onto Millipore HA 0.45 micron 96-well filter plates, pre-moistened with cold 30 mM TRIS-HCl. The filter plates are suctioned dry with vacuum and immediately washed 3× with cold 30 mM TRIS-HCl. The plates are then punched out and the amount of receptor-ligand complex is determined by liquid scintillation counting using 4 ml of Ready Protein Plus™ liquid scintillation cocktail.

IC$_{50}$ values (defined as the concentration of test compound required to decrease [$^3$H]-aldosterone binding by 50%) are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition (IC$_{50}$) of an Enzymatic Reaction, Biochem. Pharmacol., 22: 3099-31088; (1973).

Glucocorticoid Receptor Binding Assay (Method 1):

To demonstrate the GR modulating potency of compounds of the present invention the following source of glucocorticoid receptor is employed. A549 human lung epithelial cells (ATCC) are grown at a scale where gram quantity cell pellets are obtained. Harvested cell pellets are washed twice in cold phosphate buffered saline, centrifuged, and resuspended in cold assay binding buffer. The assay binding buffer consists of 10% glycerol, 50 mM Tris-HCl (pH7.2), 75 mM sodium chloride, 1.5 mM magnesium chloride, 1.5 mM EDTA, and 10 mM sodium molybdate. Cell suspensions were lysed via sonication, centrifuged, and the "extract" supernatant is snap frozen and stored at −80 C until needed.

GR binding assays are performed in a final volume of 140 ul containing 50-200 ug of A549 cell extract and 1.86 nM [$^3$H]-dexamethasone (Amersham) plus varying concentrations of test compound or vehicle. Briefly, assays are prepared at RT in 96-well Fisher 3356 plates, each well containing 100 ul of A549 cell extract, 20 ul of [$^3$H]-dexamethasone, and 20 ul of test compound/vehicle. Incubations are carried out at 4 degrees Celsius for 16 hours. After incubation, 70 ul of 3× dextran-coated charcoal solution is added to each reaction, mixed, and incubated for 8 minutes at RT. 3×-dextran-coated charcoal solution consists of 250 ml assay binding buffer, 3.75 g Norit A charcoal (Sigma), and 1.25 g dextran T-70 (Amersham). Charcoal/unbound radioligand complexes are removed by centrifugation of the plate and 140 ul of supernatant from each well is transferred to another 96 well Optiplate (Packard Instruments). 200 ul of Microscint-20 scinillant (Packard Instruments) is added to each well and amount of receptor bound radioligand is determined using Packard Instruments TopCount instrument.

$IC_{50}$ values, defined as the concentration of test compound required to decrease [$^3$H]-dexamethasone binding by 50%, are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition ($IC_{50}$) of an Enzymatic Reaction, Biochem. Pharmacol., 22: 3099-31088; (1973).

Alternative Binding Assay Protocol for MR, GR, AR, and PR (Method 2):

Cell lysates from 293 cells overexpressing human GR (glucocorticoid receptor), AR (androgen receptor), MR (mineralocorticoid receptor) or PR (progesterone receptor) are used for competition binding assays to determine Ki values for test compounds. Briefly, competition binding assays are run in a buffer containing 20 mM Hepes, pH 7.6, 0.2 mM EDTA, 75 mM NaCl, 1.5 mM MgCl2, 20% glycerol, 20 mM sodium molybdate, 0.2 mM DTT, 20 ug/ml aprotinin and 20 ug/ml leupeptin, using either 0.3 nM $^3$H-dexamethasone for GR binding, 0.36 nM $^3$H-methyltrienolone for AR binding, 0.25 nM $^3$H-aldosterone for MR binding, or 0.29 nM $^3$H-methyltrienolone for PR binding, and either 20 ug 293-GR lysate, 22 ug 293-AR lysate, 20 ug 293-MR lysate or 40 ug 293-PR lysate per well. Competing compounds are added at various concentraions in half-log increments. Non-specific binding is determined in the presence of 500 nM dexamethasone for GR binding, 500 nM aldosterone for MR binding, or 500 nM methyltrienolone for AR and PR binding,. The binding reaction (140 μl) is incubated for overnight at 40° C., then 70 μl of cold charcoal-dextran buffer (containing per 50 ml of assay buffer, 0.75 g of charcoal and 0.25 g of dextran) is added to each reaction. Plates are mixed 8 minutes on an orbital shaker at 4° C. Plates are then centrifuged at 3,000 rpm at 4° C. for 10 minutes. An aliquot of 120 μl of the mix is transferred to another 96-well plate and 175 μl of Wallac Optiphase "Hisafe 3" scintillation fluid is added to each well. Plates are sealed and shaken vigorously on an orbital shaker. After an incubation of 2 hrs, plates are read in a Wallac Microbeta counter. The data is used to calculate an IC50 and % Inhibition at 10 μM. The $K_d$ for $^3$H-dexamethasone for GR binding, $^3$H-methyltrienolone for AR binding, $^3$H-aldosterone for MR binding, or $^3$H-methyltrienolone for PR binding, is determined by saturation binding. The $IC_{50}$ values for compounds are converted to $K_i$ using Cheng-Prusoff equation and the $K_d$ determined by saturation binding assay.

Binding assay protocols for steroid hormone nuclear receptors similar to those described above can be readily designed by the ordinarily skilled artisan. U.S. Pat. No. 6,166,013 provides examples of such protocols. Representative compounds of the present invention have a Ki in the MR or GR binding assay of $\leq 50$ μM. Table I (see below) provides MR and GR binding data for a representative sample of the exemplified compounds of the present invention.

To demonstrate the ability of compounds of the present invention to modulate the activity of a steroid hormone nuclear receptor (i.e. either agonize, antagonize, partially agonize, or partially antagonize), bioassays are performed which detect modulation of target gene expression in cells transiently transfected with a nuclear receptor protein and a hormone response element-reporter gene construct. The solvents, reagents, and ligands employed in the functional assay are readily available from commercial sources, or can be synthesized by one of ordinary skill in the art.

Functional Assay of Mineralocorticoid Receptor Modulation (Method 1):

For the MR transient transfection assay, COS-7 cells are transfected with full length human MR and a 2XGRE-luciferase gene construct. Following transfection, the ability of test compounds to modulate expression of the luciferase reporter gene product is monitored. Briefly, on day one, COS cells are harvested from cell culture plates using standard procedures such as treatment with Trypsin-EDTA (GIBCO BRL): Culture medium is then added to the cells and the cell-medium mixture is plated in 96-well plates coated with poly-(d)-lysine (approximately $3 \times 10^4$ cells/well). Cells are grown for about 4 hours then transfected with Fugene-6 reagent with plasmids containing human MR, previously cloned into pc.DNA 3.1 expression vector, and 2XGRE-reporter gene construct (GRE-luciferase), previously cloned into pTAL-luc vector. Transfection is carried out in DMEM with 5% fetal calf serum, charcoal treated. 24 hours later cells are exposed to various concentrations of aldosterone in the presence and absence of test compound and incubated for an additional 24 hours. The reaction is terminated by the addition of lysis buffer followed by luciferin (luciferase substrate). Luciferase expression, as an indicator of ligand induced MR transactivation, is monitored by chemiluminescence measured using a microtiter plate luminometer (MLX). The kinetic inhibition constant ($K_b$ or $K_p$) can then be determined by analysis of dose-response curves for aldosterone, in the presence and absence of test compound, using standard techniques.

Alternative Functional Assay for MR, GR, PR and AR Activity (Method 2):

Human embryonic kidney hEK293 cells are co-transfected using Fugene. Briefly, the reporter plasmid containing two copies of GRE (glucocorticoid response element 5'TGTACAGGATGTTCT$^3$) and TK promoter upstream of the luciferase reporter cDNA, is transfected with a plasmid constitutively expressing either human glucocorticoid receptor (GR), human mineralocorticoid receptor (MR), or human progesterone receptor (PR), using viral CMV promoter. The reporter plasmid containing two copies of probasin ARE (androgen response-element 5'GGTTCTTGGAGTACT$^3$') and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 5% charcoal-stripped Fetal Bovine Serum (FBS). After a overnight incubation, transfected cells are trypsinized, plated in 96 well dishes in DMEM media containing 5% charcoal-stripped FBS, incubated for 4 h and then exposed various concentrations of test compounds in half log increments. In the antagonist assays low concentrations of agonist for each respective receptor are added to the media (0.25 nM dexamethosone for GR, 0.3 nM of methyltrienolone for AR, 0.05 nM of progesterone for PR and 0.05 nM aldosterone). After 24 h of incubations with compounds, cells are lysed and luciferase activity is determined. Data is fit to a 4 parameter-fit logistics to determine EC50 values. The % efficacy is determined versus maximum stimulation obtained with 100 nM methyltrienolone for AR assay, with 30 nM progesterone for PR assay, with 30 nM aldosterone for MR assay and with 100 nM dexamethasone for GR assay.

TABLE I

Mineralocorticoid and Glucocorticoid Receptor Binding Assay Values
(values are for racemic mixture unless otherwise indicated)

| Example No. | MR Ki (nM) Method 1 | GR Ki (nM) Method 1 | GR Ki (nM) Method 2 |
|---|---|---|---|
| 26 | +++ | +++ | — |
| 20 | +++ | +++ | — |
| 38 | +++ | +++ | — |
| 27 | +++ | +++ | — |
| 32 | +++ | +++ | — |
| 33 | +++ | +++ | — |
| 37 | +++ | +++ | — |
| 25 | +++ | +++ | — |
| 21 | +++ | +++ | — |
| 1 | +++ | +++ | — |
| 21A (isomer 1) | +++ | +++ | — |
| 21B (isomer 2) | +++ | +++ | — |
| 1A (isomer 1) | +++ | +++ | — |
| 1B (isomer 2) | +++ | +++ | — |
| 28 | +++ | +++ | — |
| 24 | +++ | +++ | — |
| 28A (isomer 1) | +++ | +++ | — |
| 28B (isomer 2) | +++ | +++ | — |
| 29 | +++ | +++ | — |
| 29A (isomer 1) | +++ | +++ | — |
| 29B (isomer 2) | +++ | +++ | — |
| 23 | +++ | +++ | — |
| 23A (isomer 1) | +++ | +++ | — |
| 23B (isomer 2) | +++ | + | — |
| 31 | +++ | +++ | — |
| 30 | +++ | — | — |
| 31A (isomer 1) | +++ | — | — |
| 31B (isomer 2) | +++ | — | — |
| 6 | +++ | — | — |
| 15 | +++ | — | — |
| 10 | ++ | — | — |
| 9 | +++ | — | — |
| 7 | +++ | — | — |
| 12 | +++ | — | — |
| 30A (isomer 1) | +++ | — | — |
| 30B (isomer 2) | +++ | — | — |
| 8 | +++ | — | — |
| 13 | — | — | — |
| 2 | +++ | — | +++ |
| 22 | +++ | — | +++ |
| 14 | +++ | — | ++ |
| 16 | +++ | — | +++ |
| 40 | +++ | — | +++ |
| 39 | +++ | — | +++ |
| 15 | — | — | +++ |
| 17 | +++ | — | +++ |
| 5 | +++ | — | +++ |
| 18 | +++ | — | +++ |
| 5 | +++ | — | ++ |
| 22A (isomer 1) | +++ | — | +++ |
| 22B (isomer 2) | +++ | — | +++ |
| 39A (isomer 1) | +++ | — | +++ |
| 39B (isomer 2) | +++ | — | +++ |
| 40A (isomer 1) | +++ | — | +++ |
| 40B (isomer 2) | +++ | — | +++ |
| 41 | +++ | — | +++ |
| 43 | — | — | + |
| 44 | +++ | — | +++ |
| 42 | +++ | — | +++ |
| 19 | +++ | — | +++ |
| 34 | +++ | — | +++ |
| 35 | +++ | — | +++ |
| 35A (isomer 1) | +++ | — | +++ |
| 35B (isomer 2) | +++ | — | +++ |
| 34A (isomer 1) | +++ | — | +++ |
| 34B (isomer 2) | +++ | — | +++ |
| 36 | +++ | — | +++ |
| 36A (isomer 1) | +++ | — | +++ |
| 36B (isomer 2) | +++ | — | +++ |

Legend:
"+" represents a value of ≦10,000 nM
"++" represents a value of ≦1,000 nM
"+++" represents a value of ≦500 nM
"—" indicates the value was not determined The following Preparations and Examples further illustrate the invention and represent typical syntheses of the compounds of Formula I, including any novel compounds, as described generally in the Schemes above. The reagents and starting materials are readily available from commercial suppliers or may be readily synthesized by one of ordinary skill in the art following the general procedures as described herein. Where the reagent or starting material is not explicitly stated, a reference to a representative Scheme describing procedures for the synthesis of said reagent or starting material is provided. It should be understood that the Preparations and Examples are set forth by way of illustration and not limitation, and that various modifications may be made by one of ordinary skill in the art.

As used herein, the following terms have the meanings indicated: "i.v." refers to intravenously; "p.o." refers to orally; "i.p." refers to intraperitoneally; "eq" or "equiv." Refers to equivalents; "g" refers to grams; "mg" refers to milligrams; "L" refers to liters; "mL" refers to milliliters; "μl" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "PPh$_3$" refers to triphenylphosphine; "DEAD" refers to diethyl azodicarboxylate; "RT" refers to room temperature; "Pd—C" refers to palladium over carbon; "SAX" refers to strong anion exchange; "SCX" refers to strong cation exchange; NaBH(Oac)$_3$ refers to sodium triacetoxyborohydride; "Bn" refers to benzyl; "BnNH$_2$" refers to benzyl amine; m-CPBA refers to meta-chloroperoxybenzoic acid; "Cbz" refers to carbobenzoxy; H$_2$ refers to hydrogen; "$K_i$" refers to the dissociation constant of an enzyme-antagonist complex and serves as an index of ligand binding; and "ID$_{50}$" and "ID$_{100}$" refer to doses of an administered therapeutic agent which produce, respectively, a 50% and 100% reduction in a physiological response.

Instrumental Analysis:

Unless otherwise indicated, $^1$H NMR spectra are recorded on a Varian Mercury 400 MHz Nuclear Magnetic Resonance (NMR) spectrometer at ambient temperature. Data are reported as follows: chemical shift (δ) in ppm from internal standard tetramethylsilane, multiplicity (b=broad, s=singlet, d=doublet, t=triplet, m=multiplet), and integration. Liquid chromatography-mass spectrometry (LC-MS) data were obtained on an Agilent 1100 Series LC/MSD instrument.

Preparation 1

1-Ethyl-5-fluoro-indan-1-ol

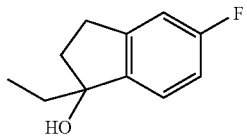

Add ethyl magnesium bromide (1.3 ml, 3.90 mmol, 1.30 equivalents, 3.0 M in tetrahydrofuran) drop wise to a solution of 5-fluoroindanone (450 mg, 3.00 mmol) in anhydrous ether (5 ml) under nitrogen at room temperature and stir overnight. Quench the reaction by drop wise addition of 10% aqueous ammonium chloride, dilute with ether, wash with water (2×), dry over anhydrous sodium sulfate, filter, and concentrate to obtain the title compound (502 mg, 93%). NMR (400 MHz, $CDCl_3$): δ 0.94 (t, 3H), 1.79 (m, 1H), 1.92 (m, 1H), 2.12 (m, 1H), 2.31 (m, 1H), 2.81 (m, 1H), 2.98 (m, 1H), 6.91 (m, 2H), 7.24 (m, 1H).

Preparation 2

(2-Carboxy-ethyl)-triphenyl-phosphonium bromide

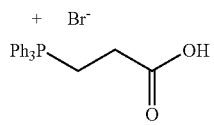

Reflux a solution of triphenylphosphine (91.3 g, 348 mmol, 1.05 equivalents) and 3-bromopropionic acid (50.7 g, 331 mmol) in acetonitrile (250 ml) for three hours, allow to sit at room temperature overnight. Add ether (400 ml) and cool in the freezer for two hours. Filter solids, rinse with ether, and dry solids under high vacuum to obtain the title compound (94.1 g, 68%). NMR (400 MHz, $CDCl_3$): δ 3.15 (m, 2H), 3.73 (m, 2H), 7.69-7.83 (m, 15H).

Preparation 3

4-(3-Fluoro-phenyl)-but-3-enoic acid

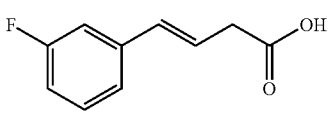

To a suspension of 3-fluoroaldehyde (13.4 ml, 126 mmol) and (2-carboxy-ethyl)-triphenyl-phosphonium bromide (62.85 g, 151 mmol, 1.20 equivalents) in anhydrous dichloromethane (150 ml) at 0° C. under nitrogen add potassium t-butoxide portion wise (315 mmol, 2.50 equivalents) over two hours and stir at room temperature overnight. Dilute with water, wash with dichloromethane (2×), acidify the aqueous layer with 1N hydrochloric acid to pH 1, dilute with ether, wash with water (2×), dry over anhydrous sodium sulfate, filter, and concentrate to obtain the title compound (24.28 g, ~99%, contains approximately 1.6 g triphenylphophine oxide). NMR (400 MHz, $CDCl_3$): δ 3.26 (d, 2H), 6.32 (m, 1H), 6.48 (d, 1H), 6.95 (t, 1H), 7.08 (d, 1H), 7.14 (d, 1H), 7.27 (m, 1H). The product is a 95:5 EZ mixture.

Preparation 4

4-(3-Fluoro-phenyl)-butyric acid

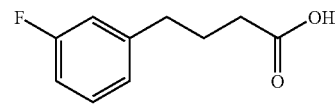

Hydrogenate a mixture of 4-(3-fluoro-phenyl)-but-3-enoic acid (22 g, 122 mmol), concentrated sulfuric acid (24 ml), and 5% palladium on carbon (3.58 g) in tetrahydrofuran (470 ml) at 60 psi at room temperature overnight. After filtration of the catalyst, remove most of the tetrahydrofuran by rotary evaporation, dilute the residue with ether, wash with water (2×), dry over anhydrous sodium sulfate, filter, and concentrate to obtain the title compound (22.50 g, 100%). NMR (400 MHz, $CDCl_3$): δ 1.98 (m, 2H), 2.38 (t, 2H), 2.65 (t, 2H), 6.88 (m, 2H), 6.96 (d, 1H), 7.23 (m, 1H).

Preparation 5

6-Fluoro-3,4-dihydro-2H-naphthalen-1-one

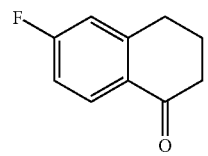

Heat a mixture of 4-(3-fluoro-phenyl)-butyric acid (1.92 g, 10.5 mmol) and polyphosphoric acid (2 g) at 110° C. under nitrogen for two hours. After cooling to room temperature, quench with water, dilute with ether, wash with saturated aqueous sodium bicarbonate (2×), dry over anhydrous sodium sulfate, and concentrate to obtain the title compound (1.51 g, 87%). NMR (400 MHz, $CDCl_3$): δ 2.16 (m, 2H), 2.64 (t, 2H), 2.97 (t, 2H), 6.92 (dd, 1H), 6.99 (dt, 1H), 8.04 (dd, 1H).

Preparation 6

5-Pyrazol-1-yl-indan-1-one

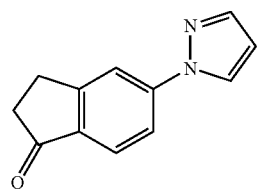

Combine 5-fluoro-indan-1-one (1.02 g, 6.79 mmol), pyrazole (0.46 g, 6.79 mmol), and potassium carbonate (1.03 g, 7.47 mmol, 1.10 equivalents) in dimethyl sulfoxide (5 ml) in a sealed tube and heat to 100° C. for 48 hours. Cool to room temperature, dilute with ether, wash with water (2×), dry over anhydrous sodium sulfate, and concentrate to obtain the title compound as a brown solid (0.98 g, 73%). LC-MS m/z 199.1 (M$^+$+1).

Preparation 7

3-(3,5-difluoro-phenyl)-propionic acid

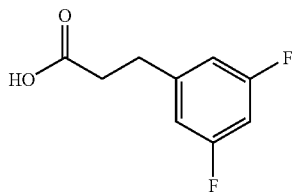

Hydrogenate a mixture of 3,5-difluorocinnamic acid (10.0 g, 54.3 mmol), 5% palladium on carbon (1.5 g), and concentrated sulfuric acid (10 ml) in tetrahydrofuran (195 ml) at 60 psi at room temperature overnight. After filtering the catalyst, dilute with ether, wash with water twice, dry over anhydrous sodium sulfate, and concentrate to obtain the title compound as clear colorless crystals (9.32 g, 92%). NMR (400 MHz, CDCl$_3$): δ 2.67 (t, 2H), 2.94 (t, 2H), 6.65 (t, 1H), 6.74 (d, 2H).

Preparation 8

1-Cyclopropyl-5-fluoro-indan-1-ol

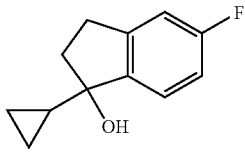

To a solution of 5-fluoroindanone (0.95 g, 6.33 mmol) in anhydrous ether (30 ml) under nitrogen at room temperature add cyclopropyl magnesium bromide (9.1 ml, 7.28 mmol, 1.15 equivalents, 0.80 M in tetrahydrofuran) dropwise while maintaining a gentle reflux. After stirring overnight, quench the reaction at room temperature via dropwise addition of 10% aqueous ammonium chloride. Dilute the reaction with ether, wash with water (2×), dry over anhydrous sodium sulfate, filter, and concentrate to give the title compound (1.30 g, ~100%). NMR (CDCl$_3$, 400 MHz): δ 0.26 (m, 1H), 0.36-0.51 (m, 3H), 1.21 (m, 1H), 2.13 (m, 1H), 2.28 (m, 1H), 2.80 (m, 1H), 2.95 (m, 1H), 6.88 (m, 2H), 7.29 (m, 1H).

Preparation 9

1H-Indol-7-ylamine

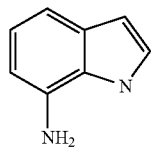

Dissolve 7-nitroindole in ethanol and add ammonium formate (10 equivalents) and a catalytic amount of 10% palladium on carbon. Heat the mixture to reflux for 1 hr before cooling, filter through celite, and evaporate to provide the product as a purple solid (99%).

Preparation 10

N-(1H-Indol-7-yl)-methanesulfonamide

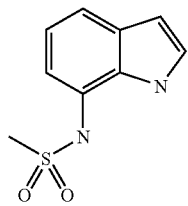

Stir 1H-indol-7-ylamine with pyridine (1 equivalent) and methanesulfonyl chloride (1 equivalent) in dichloromethane for 12 hrs. Wash the reaction with 1N hydrochloric acid and water, dry over magnesium sulfate, and evaporate. Recrystallize the residue from isopropanol to obtain the title product as a purple solid (94%). MS (ES$^+$), 210 (M), MS (ES$^-$), 209 (M−1). LC/MS shows 95% purity.

Preparation 11

3-(3-Fluorophenoxy)-propan-ol

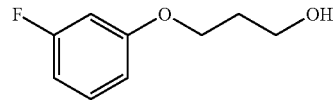

To a pre-dried round bottom flask, equipped with a magnetic stirrer, add sodium hydride (60% dispersion in mineral oil, 4.80 g, 0.120 mol) under a nitrogen atmosphere. Wash the sodium hydride with hexanes (3×100 mL) to remove the mineral oil then dimethylformamide (165 mL) is added. The resulting suspension is cooled to 0° C. and a solution of 3-fluorophenol (11.20 g, 0.100 mol) in dimethylformamide (35 mL) is added dropwise resulting in gas evolution and a color change from green to blue-green. After stirring the reaction mixture at rt for approximately 30 min the reaction is recooled to 0° C. and a solution of 3-chloro-1-propanol (9.46 g, 0.100 mol) in dimethylformamide (35 mL) is added dropwise. The resulting reaction mixture is heated to 60° C. for 2.5 h. The solution is cooled, the dimethylformamide is removed under reduced pressure and the resulting reaction mixture is diluted with water (250 mL) and extracted with diethyl ether (3×150 mL). The combined organic extracts are washed with water (200 mL), 2 M aqueous sodium hydroxide (200 mL), water (200 mL) and brine (200 mL). The organic layer is dried over magnesium sulfate, filtered and concentrated to afford the slightly impure title compound (13.32 g, 78%) as an amber oil which is used directly in the next reaction without purification: R$_f$ 0.40 (19:1 CH$_2$Cl$_2$/MeOH); $^1$H NMR (300 MHz; CDCl$_3$), δ 1.68 (t, J=5.1 Hz, 1H), 2.04 (quintuplet, J=6.0 Hz, 2H), 3.83-3.89 (m, 2H), 4.10 (t, J=6.0 Hz, 2H), 6.59-6.70 (m, 3H), 7.17-7.25 (m, 1H); $^{19}$FNMR (282 MHz, CDCl$_3$), δ-112.13; APCI MS m/z 153 [C$_9$H$_{11}$FO$_2$+H—H$_2$O]$^+$.

Preparation 12

3-(3-Fluorophenoxy)-propionic acid

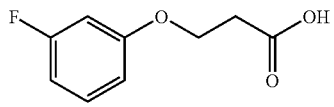

Acetone (600 mL) is chilled using an ice/salt water bath, then chromium trioxide (14.45 g, 145 mmol) is added, followed by water (32 mL) and concentrated sulfuric acid (16 mL). The mixture is allowed to stir several minutes, then a solution of 3-(3-fluorophenoxy)-propan-1-ol (6.15 g, 36.1 mmol) in acetone (300 mL) is slowly added via an addition funnel over ~1 h. The reaction is stirred at 0° C. for 5 h, and then 2-propanol (70 mL) is added. The reaction is filtered over diatomaceous earth, rinsed with acetone (~100 mL), and the filtrate evaporated under reduced pressure, reconstituted in diethyl ether (500 mL), and washed with brine (2×500 mL). The organic layer is then dried over magnesium sulfate, filtered and evaporated under reduced pressure to afford the sub-title compound (6.00 g, 90%) as an off-white solid which is used without further purification: R$_f$ 0.34 (95:5:0.5 dichloromethane/methanol/ammonium hydroxide); $^1$H NMR (300 MHz, CDCl$_3$), δ2.85 (t, J=6.2 Hz, 2H), 4.23 (t, J=6.2 Hz, 2H), 6.59-6.70 (m, 3H), 7.18-7.24 (m, 1H), 7.30-9.60 (br s, 1H); $^{19}$F NMR (282 MHz, CDCl$_3$), δ-112.01; APCI MS (negative mode) m/z 183 [C$_9$H$_9$FO$_3$—H]$^-$.

Preparation 13

7-Fluoro-chroman-4-one

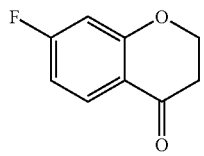

To a solution of 3-(3-fluorophenoxy)-propionic acid (4.94 g, 26.8 mmol) in dichloromethane (135 mL) is added several drops of anhydrous dimethylformamide, followed by oxalyl chloride (4.68 mL, 53.6 mmol). The reaction is stirred at room temperature until gas evolution ceases (~30 min), then evaporated under reduced pressure and reconstituted in dichloromethane (135 mL). Following the addition of aluminum trichloride (4.28 g, 32.1 mmol), the reaction is stirred for 1 h, then 2 M aqueous hydrochloric acid (100 mL) and dichloromethane (100 mL) are added. The layers are separated, and the aqueous layer extracted with dichloromethane (2×100 mL). The combined organic-layers are washed with brine (2×100 mL), dried over magnesium sulfate, filtered and evaporated under reduced pressure. The crude residue is recrystallized twice from 2-propanol to afford slightly impure title compound (1.79 g, 40%), and the mother liquor subjected to flash chromatography (silica gel, 3:1 pentane/Et$_2$O) to afford pure title compound (1.15 g, 26%): R$_f$ 0.45 (1:1 ethyl acetate/hexanes); mp 53-56 ° C.; $^1$H NMR (300 MHz, CDCl$_3$), δ2.75 (t, J=6.4 Hz, 2H), 4.51 (t, J=6.4 Hz, 2H), 6.61 (dd, J=2.3, 9.9 Hz, 1H), 6.65-6.72 (m, 1H), 7.87 (dd, J=6.7, 8.8 Hz, 1H); $^{19}$F NMR (282 MHz, CDCl$_3$), δ-101.06; APCI MS m/z 167 [C$_9$H$_7$FO$_2$+H]$^+$.

Preparation 14

1H-Indol-7-ylamine

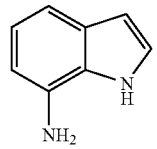

Charge a 3-gal autoclave with 7-nitroindole (250 g, 1.542 moles), 2B-3 ethyl alcohol (5.0 L), and 10% Pd/C (50.0 g). Stir at 50 psi H$_2$ for 2 h at <27° C. When the reaction is deemed complete, filter the reactor contents through Celite followed by concentration of the filtrate to dryness to yield 197.0 g (96.7%) of the title compound as purple solid. $^1$H-NMR(CD$_3$OD, 300 MHz), δ 7.16 (d, 1H), 7.00 (dd, 1H), 6.81 (t, 1H), 6.50 (dd, 1H), 6.37 (d, 1H).

Preparation 15

(1H-Indol-7-yl)-carbamic acid benzyl ester

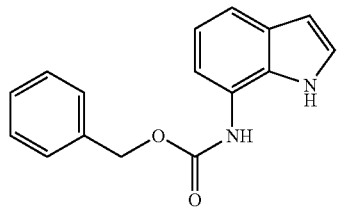

Equip a 12-L reaction flask with a cooling bath, air driven stirring apparatus, addition funnel, and thermometer probe. Thoroughly purge the flask with nitrogen, charge 7-aminoindole (352 g, 2.663 moles), CH$_2$Cl$_2$ (5.30 L, 15 volumes) and 2N NaOH (1.76 L, 3.515 moles). After cooling the biphasic solution to less than 10° C., benzyl chloroformate (500 g, 2.929 moles) add dropwise at such a rate so as to maintain the temperature at less than 10° C. over one hour. Stir the reaction vigorously for 1 hour until complete by TLC. Separate the layers and extract the aqueous layer with CH$_2$Cl$_2$ (1.7 L). Combine the organic layers, wash with 2N NaOH (2×2 L), and dry over Na$_2$SO$_4$. After filtering off the drying agent, concentrate the filtrate in vacuo to a volume of ~1.5 L resulting in thin dark mixture. Gradually exchange the solvent using heptane (~4 L) to form a thick sand-like slurry and increase the bath temperature to 50-60° C. Concentrate to a volume of ~1.5 L, filter while hot (50-60° C.), wash with warm (45° C.) heptane (1 L) and RT heptane (1 L), and dry to yield 683.5 g (96.7%) of the title compound as light purple solid. $^1$H-NMR(DMSO-d6, 300 MHz), δ 10.79 (br s, 1H), 9.42 (br s, 1H), 7.20-7.56 (m, 8H), 6.92 (t, 1H), 6.41 (dd, 1H), 5.18(s, 1H).

EXAMPLE 1

N-[3-(1-ethyl-5-fluoro-indan-1-yl)-1H-indol-7-yl]-methanesulfonamide

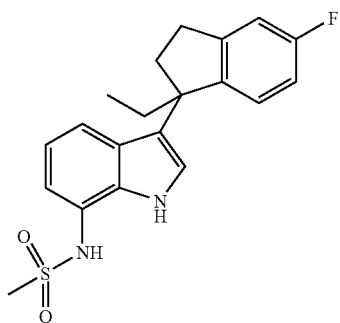

Combine 1-ethyl-5-fluoro-indan-1-ol (502 mg, 2.79 mmol, 1.30 equivalents), N-(1H-Indol-7-yl)-methanesulfonamide (450 mg, 2.14 mmol, 1.00 equivalents), and trifluoroacetic acid (0.25 ml, 3.21 mmol, 1.50 equivalents) in dichloromethane (5 ml) and stir at room temperature under nitrogen overnight. Load the solution on silica and purify eluting with 0 to 100% ethyl acetate/hexanes over 25 minutes to obtain the title compound (672 mg, 84%). LC-MS m/z 373.0 ($M^+$+1). The racemic mixture is separated on a Chiralcel OJ 8×33 cm column eluting with methanol with 0.2% dimethylethylamine (flow: 375 ml/min, UV detection at 230 nm) to provide the individual enantiomers, Examples 1A and 1B, in 96.3% ee and 97.4% ee, respectively.

EXAMPLE 2

3-(1-Ethyl-5-fluoro-indan-1-yl)-7-nitro-1H-indole

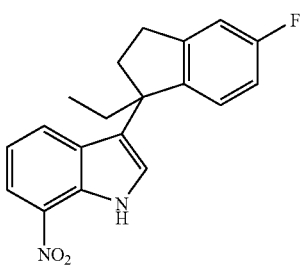

Utilizing 1-ethyl-5-fluoro-indan-1-ol and 7-nitroindole, the title compound is prepared as in example 1. 0.37 g (42%). NMR (400 MHz, $CDCl_3$): δ 0.85 (t, 3H), 2.18 (m, 2H), 2.35 (m, 1H), 2.53 (m, 1H), 3.00 (m, 2H), 6.83 (t, 1H), 6.92 (t, 1H), 7.01 (m, 2H), 7.08 (s, 1H), 7.44 (d, 1H), 8.09 (d, 1H), 9.76 (s, 1H, NH).

EXAMPLE 3

3-(1-Ethyl-5-fluoro-indan-1-yl)-1-methyl-7-nitro-1H-indole

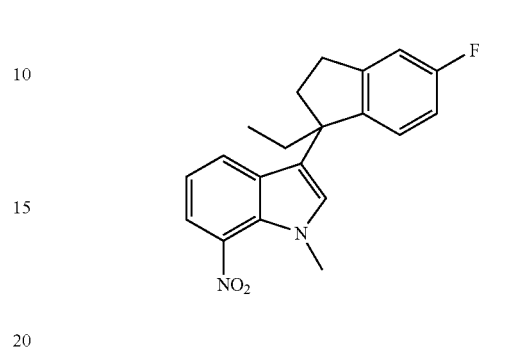

Combine 3-(1-ethyl-5-fluoro-indan-1-yl)-7-nitro-1H-indole (0.33 g, 1.02 mmol), sodium methoxide (110 mg, 2.04 mmol), and iodomethane (0.10 ml, 1.53 mmol) in dimethylformamide (5 ml) and stir at room temperature under nitrogen overnight. Dilute with ether, wash with water (2×), dry over sodium sulfate, filter, and concentrate to obtain the title compound as a yellow amorphous solid (0.33 g, 94%). LC-MS m/z 339.1 ($M^+$+1).

EXAMPLE 4

3-(1-Ethyl-5-fluoro-indan-1-yl)-1-methyl-1H-indol-7-ylamine

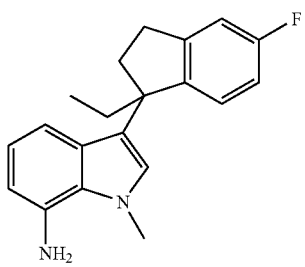

Hydrogenate a mixture of 3-(1-ethyl-5-fluoro-indan-1-yl)-1-methyl-7-nitro-1H-indole (0.26 g, 0.77 mmol) and 5% palladium on carbon (26 mg) in ethanol (50 ml) at 60 psi at room temperature overnight. Filter catalyst and concentrate under high vacuum to obtain the title compound as oil (0.17 g, 71%). NMR (400 MHz, $CDCl_3$): δ 0.83 (t, 3H), 2.05 (m, 1H), 2.25 (m, 2H), 2.60 (m, 1H), 2.96 (m, 2H), 3.72 (broad s, 2H, NH2), 4.02 (s, 3H), 6.43 (m, 2H), 6.76 (d, 2H), 6.83 (t, 1H), 6.97 (d, 1H), 7.02 (m, 1H).

EXAMPLE 5

N-[3-(1-Ethyl-5-fluoro-indan-1-yl)-1-methyl-1H-indol-7-yl]-methanesulfonamide

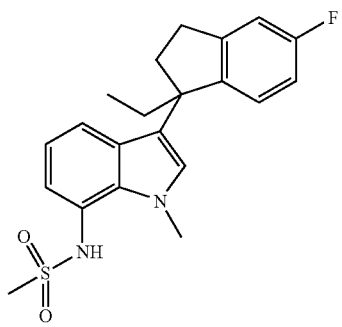

Dissolve 3-(1-ethyl-5-fluoro-indan-1-yl)-1-methyl-1H-indol-7-ylamine (0.18 g, 0.58 mmol) in pyridine (3 ml). Add methanesulfonyl chloride (0.05 ml, 0.70 mmol, 1.20 equivalents) and stir at room temperature under nitrogen overnight. Dilute with ether, wash with 1N aqueous hydrochloric acid (2×), dry over anhydrous sodium sulfate, filter, and concentrate solution in vacuo. Purify the residue on silica eluting with 0 to 100% ethyl acetate/hexanes over 25 minutes to provide the title compound as a white solid (0.19 g, 86%). LC-MS m/z 387.1 (M$^+$+1).

EXAMPLE 6

3-(1-Ethyl-5-fluoro-indan-1-yl)-1H-indole

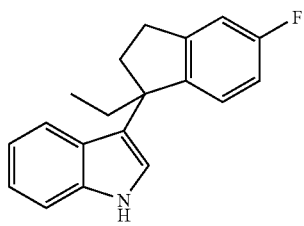

Utilizing 1-ethyl-5-fluoro-indan-1-ol and indole, the title compound is prepared as in example 1. 89 mg (54%). LC-MS m/z 280.0 (M$^+$+1).

EXAMPLE 7

3-(1-Ethyl-5-fluoro-indan-1-yl)-7-fluoro-1H-indole

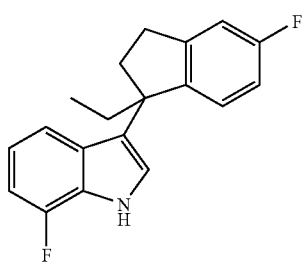

Utilizing 1-ethyl-5-fluoro-indan-1-ol and 7-fluoroindole, the title compound is prepared as in example 1. 217 mg (92%). NMR (400 MHz, CDCl$_3$): δ 0.85 (t, 3H), 2.12 (m, 1H), 2.21 (m, 1H), 2.31 (m, 1H), 2.58 (m, 1H), 2.97 (m, 2H), 6.83 (m, 4H), 6.98 (m, 3H), 8.06 (s, 1H, NH).

EXAMPLE 8

7-Bromo-3-(1-ethyl-5-fluoro-indan-1-yl)-1H-indole

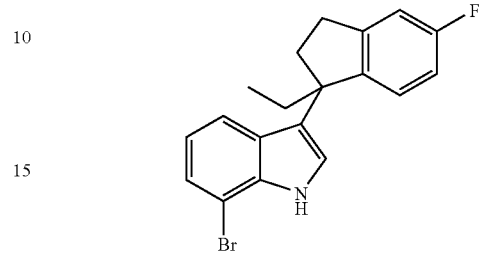

Utilizing 1-ethyl-5-fluoro-indan-1-ol and 7-bromoindole, the title compound is prepared as in example 1. 51 mg (16%). NMR (400 MHz, CDCl$_3$): δ 0.82 (t, 3H), 2.12 (m, 1H), 2.21 (m, 1H), 2.30 (m, 1H), 2.59 (m, 1H), 2.97 (m, 2H), 6.82 (m, 2H), 6.90 (s, 1H), 6.99 (m, 2H), 7.12 (d, 1H), 7.28 (d, 1H), 8.08 (s, 1H, NH).

EXAMPLE 9

7-Chloro-3-(1-ethyl-5-fluoro-indan-1-yl)-1H-indole

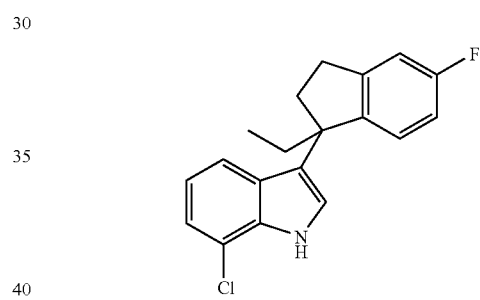

Utilizing 1-ethyl-5-fluoro-indan-1-ol and 7-chloroindole, the title compound is prepared as in example 1. 90 mg (60%). NMR (400 MHz, CDCl$_3$): δ 0.85 (t, 3H), 2.15 (m, 1H), 2.22 (m, 1H), 2.34 (m, 1H), 2.59 (m, 1H), 2.98 (m, 2H), 6.82 (t, 1H), 6.87 (m, 2H), 7.00 (m, 2H), 7.11 (d, 1H), 7.16 (d, 1H), 8.12 (s, 1H, NH).

EXAMPLE 10

7-Ethyl-3-(1-ethyl-5-fluoro-indan-1-yl)-1H-indole

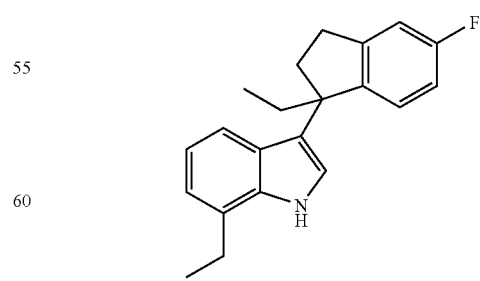

Utilizing 1-ethyl-5-fluoro-indan-1-ol and 7-ethylindole, the title compound is prepared as in example 1. 104 mg (58%). LC-MS m/z 308.1 (M$^+$+1).

EXAMPLE 11

3-(1-Ethyl-5-fluoro-indan-1-yl)-1H-indole-7-carboxylic acid methyl ester

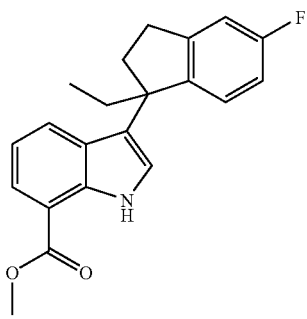

Utilizing 1-ethyl-5-fluoro-indan-1-ol and 1H-indole-7-carboxylic acid methyl ester, the title compound is prepared as in example 1. 103 mg (75%). LC-MS m/z 338.1 (M$^+$+1).

EXAMPLE 12

3-(1-Ethyl-5-fluoro-indan-1-yl)-7-methoxy-1H-indole

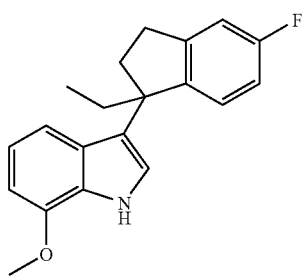

Utilizing 1-ethyl-5-fluoro-indan-1-ol and 7-methoxyindole, the title compound is prepared as in example 1. 123 mg (59%). LC-MS m/z 310.2 (M$^+$+1).

EXAMPLE 13

[3-(1-Ethyl-5-fluoro-indan-1-yl)-1H-indol-7-yl]-carbamic acid benzyl ester

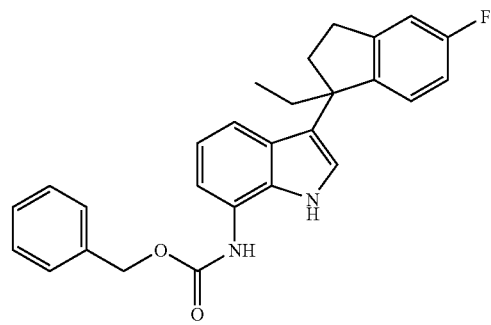

Utilizing 1-ethyl-5-fluoro-indan-1-ol and (1H-indol-7-yl)-carbamic acid benzyl ester, the title compound is prepared as in example 1. 7.78 g (100%). LC-MS m/z 249.1 (M$^+$+1)

EXAMPLE 14

3-(1-Ethyl-5-fluoro-indan-1-yl)-1H-indol-7-ylamine

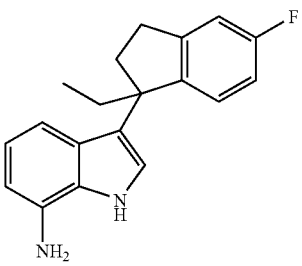

A mixture of [3-(1-ethyl-5-fluoro-indan-1-yl)-1H-indol-7-yl]-carbamic acid benzyl ester (7.78 g, 18.2 mmol) and 20% palladium hydroxide on carbon (1.6 g) in ethanol is hydrogenated at 50° C. at 60 psi for 18 hours. After filtration of the catalyst the solution is concentrated in vacuo to furnish the title compound as a black solid (5.04 g, 94%). LC-MS m/z 295.1 (M$^+$+1).

EXAMPLE 15

[3-(1-Ethyl-5-fluoro-indan-1-yl)-1H-indol-7-yl]-carbamic acid methyl ester

Dissolve 3-(1-ethyl-5-fluoro-indan-1-yl)-1H-indol-7-ylamine (0.35 g, 1.19 mmol) in pyridine (3 ml). Add methyl chloroformate (0.10 ml, 1.31 mmol, 1.1 equivalents) and stir at room temperature under nitrogen overnight. Dilute with ether, wash with 1N aqueous hydrochloric acid (2×), dry over anhydrous sodium sulfate, filter, and concentrate solution in vacuo. Purify the residue on silica eluting with 0 to 75% ethyl acetate/hexanes over 30 minutes to provide the title compound as a white solid (0.15 g, 36%). LC-MS m/z 353.1 (M$^+$+1).

EXAMPLE 16

N-[3-(1-ethyl-5-fluoro-indan-1-yl)-1H-indol-7-yl]-acetamide

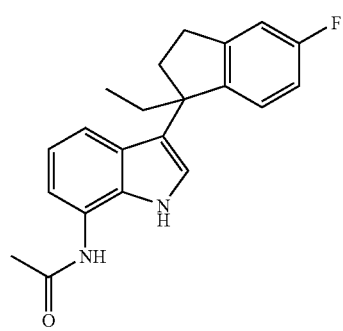

Utilizing 3-(1-ethyl-5-fluoro-indan-1-yl)-1H-indol-7-ylamine and acetic anhydride, the title compound is prepared as in example 15. 0.16 g (46%). LC-MS m/z 337.1 (M$^+$+1).

EXAMPLE 17

7-Dimethylsulfamoyl-3-(1-ethyl-5-fluoro-indan-1-yl)-1H-indole

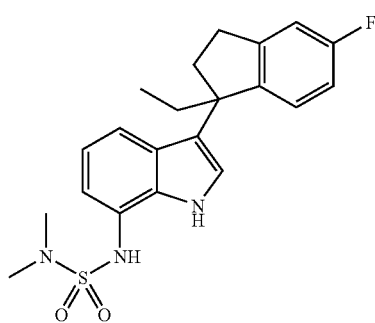

Utilizing 3-(1-ethyl-5-fluoro-indan-1-yl)-1H-indol-7-ylamine and dimethyl sulfamoyl chloride, the title compound is prepared as in example 15. 0.16 g (29%). LC-MS m/z 402.1 (M$^+$+1).

EXAMPLE 18

N-[3-(1-ethyl-5-fluoro-indan-1-yl)-1H-indol-7-yl]-benzenesulfonamide

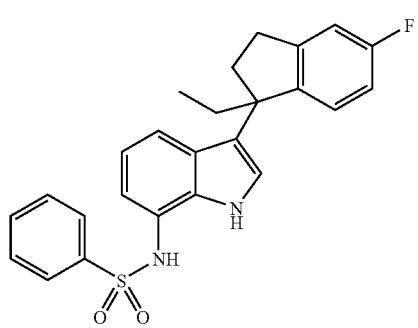

Utilizing 3-(1-ethyl-5-fluoro-indan-1-yl)-1H-indol-7-ylamine and benzenesulfonyl chloride, the title compound is prepared as in example 15. 0.21 g (33%). LC-MS m/z 295.1 (M$^+$+1).

EXAMPLE 19

Ethanesulfonic acid [3-(1-ethyl-5-fluoro-indan-1-yl)-1H-indol-7-yl]-amide

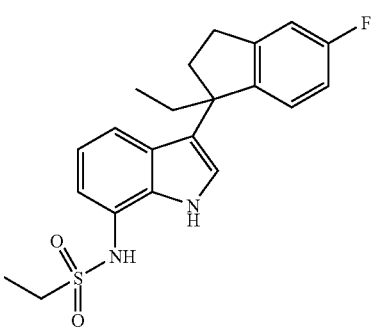

Utilizing 3-(1-ethyl-5-fluoro-indan-1-yl)-1H-indol-7-ylamine and ethanesulfonyl chloride, the title compound is prepared as in example 15. 0.18 g (35%). LC-MS m/z 387.1 (M$^+$+1).

The carbinols used in Examples 20-39 are prepared from the appropriate ketone as in Preparation 1.

EXAMPLE 20

N-[3-(1-Methyl-indan-1-yl)-1H-indol-7-yl]-methanesulfonamide

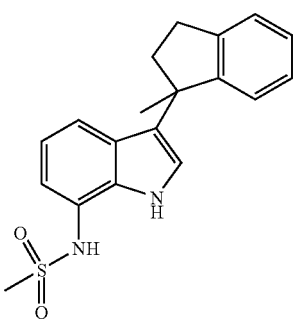

Utilizing the appropriate carbinol and N-(1H-Indol-7-yl)-methanesulfonamide, the title compound is prepared as in Example 1. 634 mg (74%). LC-MS m/z 341.1 (M$^+$+1).

EXAMPLE 21

N-[3-(5-Fluoro-1-methyl-indan-1-yl)-1H-indol-7-yl]-methanesulfonamide

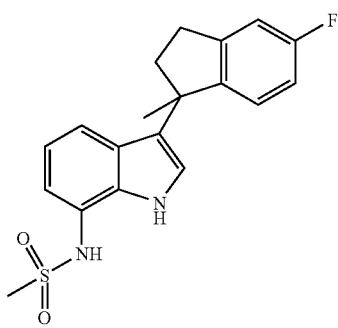

Utilizing the appropriate carbinol and N-(1H-Indol-7-yl)-methanesulfonamide, the title compound is prepared as in Example 1. 737 mg (83%). LC-MS m/z 359.1 (M$^+$+1). The racemic mixture is separated on a Chiralcel OJ 8×33 cm column eluting with 15/85 acetonitrile/methanol with 0.2% dimethylethylamine (flow: 400 ml/min, UV detection at 275 nm) to give the individual enantiomers, Examples 21A and 21B, in greater than 99.9% ee and 97.4% ee, respectively.

EXAMPLE 22

N-[3-(5,7-Difluoro-1-methyl-indan-1-yl)-1H-indol-7-yl]-methanesulfonamide

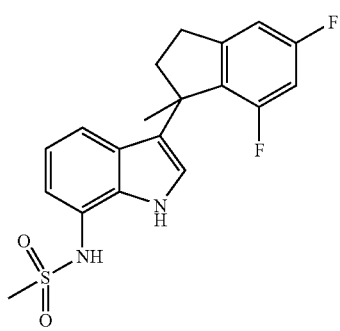

Utilizing the appropriate carbinol and N-(1H-Indol-7-yl)-methanesulfonamide, the title compound is prepared as in Example 1. 1.25 g (71%). LC-MS m/z 377.1 (M$^+$+1). The racemic mixture is separated on a Chiralcel OJ 8×33 cm column eluting with 20/20/60 3A alcohol/methanol/heptane with 0.2% dimethylethylamine (flow: 375 ml/min, UV detection at 300 nm) to provide the individual enantiomers, Examples 22A and 22B, in 99.3% ee and 99.6% ee, respectively.

EXAMPLE 23

N-[3-(1-Ethyl-5,7-difluoro-indan-1-yl)-1H-indol-7-yl]-methanesulfonamide

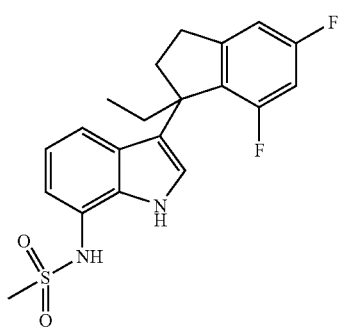

Utilizing the appropriate carbinol and N-(1H-Indol-7-yl)-methanesulfonamide, the title compound is prepared as in Example 1. 0.41 g (69%). LC-MS m/z 391.0 (M$^+$+1). The racemic mixture is separated on a Chiralcel OD 8×34 cm column eluting with 30/10/60 isopropanol/methanol/heptane with 0.2% dimethylethylamine (flow: 375 ml/min, UV detection at 300 nm) to give the individual enantiomers, Examples 23A and 23B, in 97.2% ee and 98.5% ee, respectively.

EXAMPLE 24

N-[3-(1-Methyl-5-pyrazol-1-yl-indan-1-yl)-1H-indol-7-yl]-methanesulfonamide

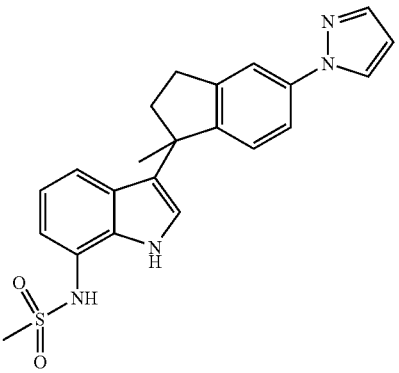

Utilizing the appropriate carbinol and N-(1H-Indol-7-yl)-methanesulfonamide, the title compound is prepared as in Example 1. 0.43 g (32%). LC-MS m/z 407.1 (M$^+$+1).

EXAMPLE 25

N-[3-(1,2,3,4-Tetrahydro-naphthalen-1-yl)-1H-indol-7-yl]-methanesulfonamide

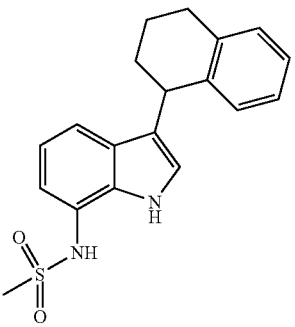

Utilizing the appropriate carbinol and N-(1H-Indol-7-yl)-methanesulfonamide, the title compound is prepared as in Example 1. 197 mg (40%). LC-MS m/z 341.1 (M$^+$+1).

EXAMPLE 26

N-[3-(1-Methyl-1,2,3,4-tetrahydro-naphthalen-1-yl)-1H-indol-7-yl]-methanesulfonamide

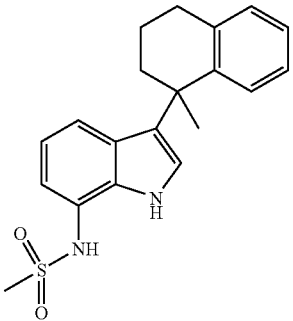

Utilizing the appropriate carbinol and N-(1H-Indol-7-yl)-methanesulfonamide, the title compound is prepared as in Example 1. 541 mg (78%). LC-MS m/z 355.0 (M$^+$+1).

EXAMPLE 27

N-[3-(1-Ethyl-1,2,3,4-tetrahydro-naphthalen-1-yl)-1H-indol-7-yl]-methanesulfonamide

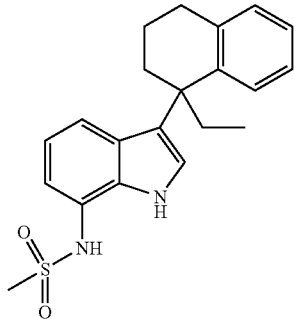

Utilizing the appropriate carbinol and N-(1H-Indol-7-yl)-methanesulfonamide, the title compound is prepared as in Example 1. 140 mg (54%). LC-MS f/z 369.1 (M$^+$+1).

EXAMPLE 28

N-[3-(6-Fluoro-1-methyl-1,2,3,4-tetrahydro-naphthalen-1-yl)-1H-indol-7-yl]-methanesulfonamide

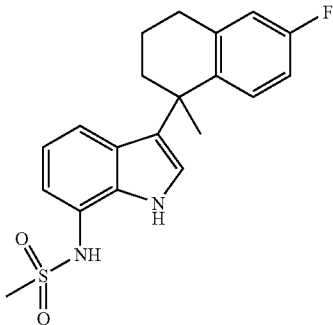

Utilizing the appropriate carbinol and N-(1H-Indol-7-yl)-methanesulfonamide, the title compound is prepared as in Example 1. 0.81 g (76%). LC-MS m/z 373.2 (M$^+$+1). The racemic mixture is separated on a Chiralcel OJ 8×33 cm column eluting with 20/80 acetonitrile/methanol with 0.2% dimethylethylamine (flow: 375 ml/min, UV detection at 316 nm) to provide the individual enantiomers, Examples 28A and 28B, in greater than 99.9% ee and greater than 99.9% ee, respectively.

EXAMPLE 29

N-[3-(1-Ethyl-6-fluoro-1,2,3,4-tetrahydro-naphthalen-1-yl)-1H-indol-7-yl]-methanesulfonamide

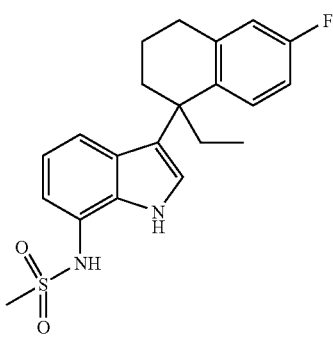

Utilizing the appropriate carbinol and N-(1H-Indol-7-yl)-methanesulfonamide, the title compound is prepared as in Example 1, 2.23 g (74%). NMR (400 MHz, CDCl$_3$): δ 0.89 (t, 3H), 1.62-1.86 (m, 2H), 2.05 (m, 1H), 2.16-2.42 (m, 4H), 2.84 (t, 2H), 3.01 (s, 3H), 6.42 (s, 1H), 6.70 (s, 1H), 6.75 (t, 1H), 6.82-6.93 (m, 3H), 7.05 (m, 1H), 7.21 (d, 1H), 8.91 (broad s, 1H, NH). The racemic mixture is separated on a Chiralpak AD 8×30 cm column eluting with 100% 3A alcohol with 0.2% dimethylethylamine (flow: 300 ml/min, UV detection at 270 nm) to provide the individual enantiomers, Examples 29A and 29B, in 99.5% ee and 99.6% ee, respectively.

EXAMPLE 30

N-[3-(6,8-Difluoro-1-methyl-1,2,3,4-tetrahydro-naphthalen-1-yl)-1H-indol-7-yl]-methanesulfonamide

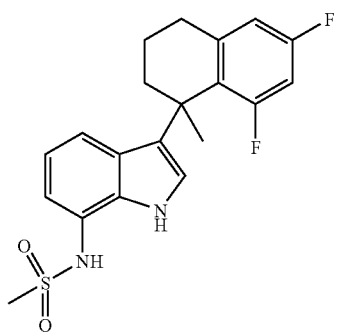

Utilizing the appropriate carbinol and N-(1H-Indol-7-yl)-methanesulfonamide, the title compound is prepared as in Example 1. 3.12 g (68%). LC-MS m/z 391.0 (M$^+$+1). The racemic mixture is separated on a Chiralcel OJ 8×33 cm column eluting with 5/95 acetonitrile/methanol (flow: 375 ml/min, UV detection at 225 nm) to give the individual enantiomers, Examples 31A and 31B, in greater than 99.9% ee and 99.3% ee, respectively.

EXAMPLE 31

N-[3-(1-Ethyl-6,8-difluoro-1,2,3,4-tetrahydro-naphthalen-1-yl)-1H-indol-7-yl]-methanesulfonamide

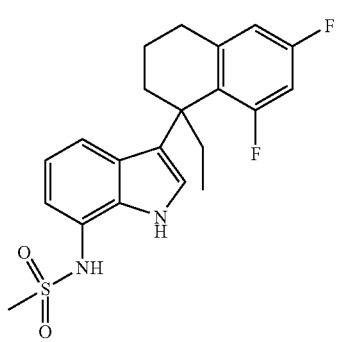

Utilizing the appropriate carbinol and N-(1H-Indol-7-yl)-methanesulfonamide, the title compound is prepared as in Example 1. 380 mg (40%). NMR (400 MHz, CDCl$_3$): δ 0.82 (t, 3H), 1.58-1.78 (m, 2H), 2.08 (m, 1H), 2.17 (m, 1H), 2.40 (m, 1H), 2.55 (m, 1H), 2.82 (m, 2H), 3.01 (s, 3H), 6.47 (s, 1H), 6.57 (t, 1H), 6.67 (s, 1H), 6.74 (d, 1H), 6.87 (d, 1H), 6.94 (t, 1H), 7.31 (d, 1H), 8.94 (broad s, 1H, NH). The racemic mixture is separated on a Chiralcel OJ 8×33 cm column eluting with 5/95 acetonitrile/methanol (flow: 375 ml/min, UV detection at 230 nm) to give the individual enantiomers, Examples 31A and 31B, in greater than 99.9% ee and 99.5% ee, respectively.

EXAMPLE 32

N-[3-(4-Methyl-chroman-4-yl)-1H-indol-7-yl]-methanesulfonamide

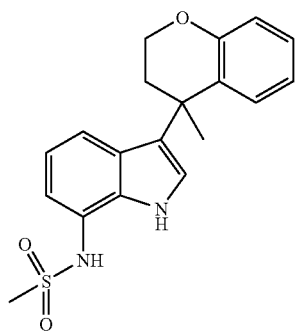

Utilizing the appropriate carbinol and N-(1H-Indol-7-yl)-methanesulfonamide, the title compound is prepared as in Example 1. 226 mg (99%). LC-MS m/z 357.0 (M$^+$+1).

EXAMPLE 33

N-[3-(6-Fluoro-4-methyl-chroman-4-yl)-1H-indol-7-yl]-methanesulfonamide

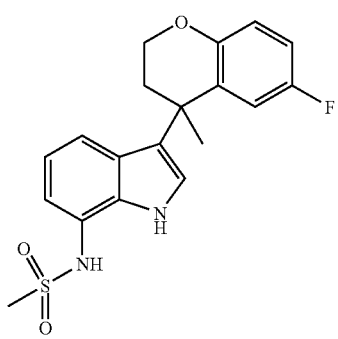

Utilizing the appropriate carbinol and N-(1H-Indol-7-yl)-methanesulfonamide, the title compound is prepared as in Example 1. 270 mg (99%). LC-MS m/z 375.0 (M$^+$+1).

EXAMPLE 34

N-[3-(7-Fluoro-4-methyl-chroman-4-yl)-1H-indol-7-yl]-methanesulfonamide

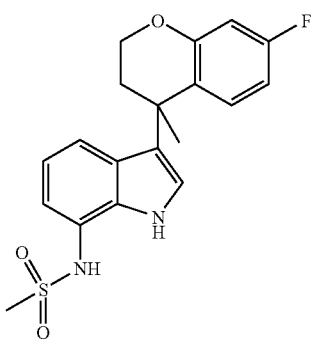

Utilizing the appropriate carbinol and N-(1H-Indol-7-yl)-methanesulfonamide, the title compound is prepared as in Example 1. 3.6 g (100%). LC-MS m/z 375.0(M$^+$+1). The racemic mixture is separated on a Chiralpak AD 8×30 cm column eluting with 100% 3A alcohol (flow: 375 ml/min, UV detection at 230 nm) to give the individual enantiomers, Examples 34A and 34B, in 98.9% ee and 99.1% ee, respectively.

EXAMPLE 35

N-[3-(4-Ethyl-7-fluoro-chroman-4-yl)-1H-indol-7-yl]-methanesulfonamide

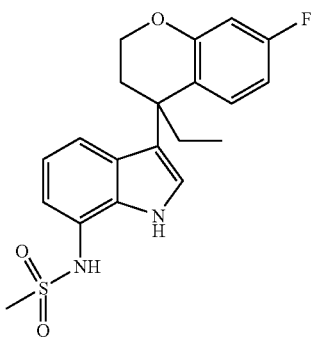

Utilizing the appropriate carbinol and N-(1H-Indol-7-yl)-methanesulfonamide, the title compound is prepared as in Example 1. 3.85 g (99%). LC-MS m/z 389.1 (M$^+$+1). The racemic mixture is separated on a Chiralcel OJ 8×33 cm column eluting with 10/90 acetonitrile/methanol (flow: 375 ml/min, UV detection at 230 nm) to give the individual enantiomers, Examples 35A and 35B, in 96.5% ee and 98.2% ee, respectively.

EXAMPLE 36

N-[3-(4-Ethyl-5,7-difluoro-chroman-4-yl)-1H-indol-7-yl]-methanesulfonamide

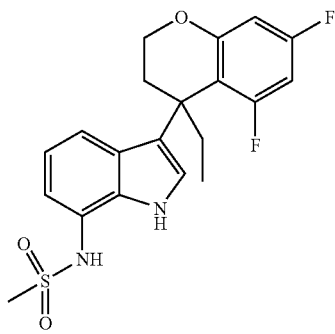

Utilizing the appropriate carbinol and N-(1H-Indol-7-yl)-methanesulfonamide, the title compound is prepared as in Example 1. 4.13 g (94%). LC-MS m/z 407.0 (M$^+$+1). The racemic mixture is separated on a Chiralcel OJ 8×33 cm column eluting with 20/80 acetonitrile/methanol with 0.2% dimethylethylamine (flow: 375 ml/min, UV detection at 280 nm) to give the individual enantiomers, Examples 36A and 36B, in greater than 99.9% ee and 99.9% ee, respectively.

EXAMPLE 37

N-[3-(4-Methyl-thiochroman-4-yl)-1-indol-7-yl]-methanesulfonamide

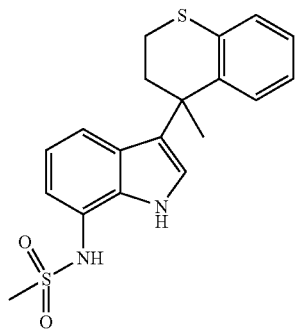

Utilizing the appropriate carbinol and N-(1H-Indol-7-yl)-methanesulfonamide, the title compound is prepared as in Example 1. 195 mg (74%). LC-MS m/z 390.1 (M$^+$+H$_2$O).

EXAMPLE 38

N-[3-(5-Methyl-6,7,8,9-tetrahydro-5H-benzocyclo-hepten-5-yl)-1H-indol-7-yl]-methanesulfonamide

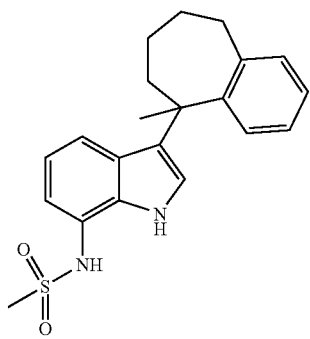

Utilizing the appropriate carbinol and N-(1H-Indol-7-yl)-methanesulfonamide, the title compound is prepared as in Example 1. 213 mg (66%). NMR (400 MHz, CDCl$_3$): δ 1.47 (m, 1H), 1.75 (m, 1H), 1.78 (s, 3H), 1.87 (m, 3H), 2.60 (m, 1H), 2.67 (m, 1H), 2.79 (m, 1H), 6.43 (s, 1H), 6.67 (s, 1H), 6.87 (d, 1H), 6.93 (t, 1H), 7.11 (m, 1H), 7.16-7.21 (m, 3H), 7.41 (m, 1H), 8.91 (broad s, 1H, NH).

EXAMPLE 39

N-[3-(1-Cyclopropyl-5-fluoro-indan-1-yl)-1H-indol-7-yl]-methanesulfonamide

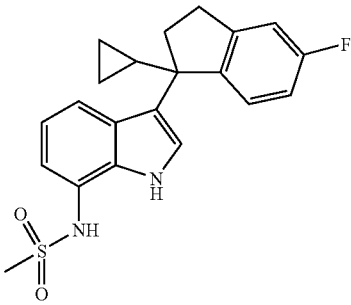

Combine N-(1H-Indol-7-yl)-methanesulfonamide (0.95 g, 4.51 mmol), 1-cyclopropyl-5-fluoro-indan-1-ol (1.30 g, 6.76 mmol, 1.50 equivalents), and trifluoroacetic acid (0.70 ml, 9.02 mmol, 2.00 equivalents) in dichloromethane (20 ml) and stir at room temperature under nitrogen overnight. Preload the solution on silica and purify on 40 g of silica eluting with 0 to 50 ethyl acetate/hexanes over 30 minutes. Isolate the product as a white crystalline solid (1.42 g). NMR analysis indicates a one to one mixture of the title compound and propyl-trifluoroacetate ester. Dissolve the product in methanol (20 ml) and 2M aqueous lithium hydroxide (20 ml) and stir at room temperature overnight. Dilute with ether, wash with 1N hydrochloric acid (2x), dry over sodium sulfate, filter, and concentrate. Purify on 40 g of silica eluting with 0 to 100 ethyl acetate/hexanes over 30 minutes to obtain the title compound as a white solid (0.39 g). The title compound is the less polar component. NMR (400 MHz, CDCl$_3$): δ 1.47 (m, 1H), −0.15 (m, 1H), 0.11 (m, 1H), 0.49 (m, 2H), 1.45 (m, 1H), 2.21 (m, 1H), 2.67 (m, 1H), 2.94 (m, 1H), 3.01 (s, 3H), 3.05 (m, 1H), 6.55 (s, 1H), 6.72 (m, 2H), 6.83 (m, 3H), 6.97 (d, 1H), 7.33.(s, 1H), 9.02 (broad s, 1H, NH). The racemic mixture is separated on a Chiralcel OJ 8×33 cm column eluting with 60/40 acetonitrile/methanol with 0.2% dimethylethylamine (flow: 375 ml/min, UV detection at 275 nm) to give the individual enantiomers, Examples 39A and 39B, in greater than 99.9% ee and 99.6% ee, respectively.

EXAMPLE 40

N-{3-[5-Fluoro-1-(3-hydroxy-propyl)-indan-1-yl]-1H-indol-7-yl}-methanesulfonamide

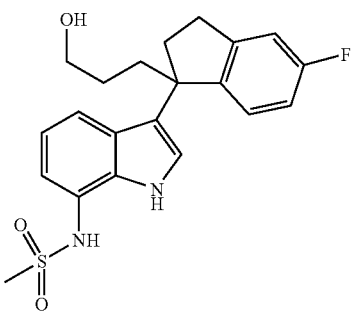

The title compound is the more polar component of the final chromatography described in example 39. NMR (400

MHz, CDCl₃): δ 1.47-1.60 (m, 2H), 2.08-2.29 (m, 3H), 2.58 (m, 1H), 2.97 (m, 2H), 2.99 (s, 3H), 2.61 (m, 2H), 6.77 (t, 1H), 6.85-6.98 (m, 6H), 7.05 (d, 1H), 9.01 (broad s, 1H, NH). The racemic mixture is separated on a Chiralpak AD 8×30 cm column eluting with 40/10/50 isopropanol/methanol/heptane with 0.2% dimethylethylamine (flow: 350 ml/min, UV detection at 232 nm) to give the individual enantiomers, Examples 40A and 40B, in 98.2% ee and 96.8% ee, espectively.

EXAMPLE 41

N-{3-[5-Fluoro-1-(3-iodo-propyl)-indan-1-yl]-1H-indol-7-yl}-methanesulfonamide

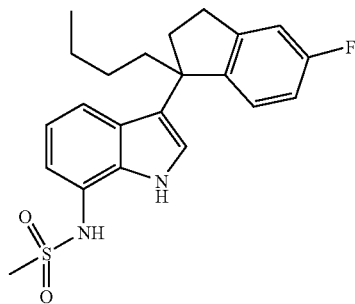

To a solution of triphenylphosphine (422 mg, 1.61 min ol, 1.30 equivalents) and imidazole (219 mg, 3.22 mmol, 2.60 equivalents) in anhydrous tetrahydrofuran (10 ml) add iodine (410 mg, 1.61 mmol, 1.30 equivalents). After stirring for 20 minutes at room temperature under nitrogen, add N-{3-[5-Fluoro-1-(3-hydroxy-propyl)-indan-1-yl]-1H-indol-7-yl}-methanesulfonamide (500 mg, 1.24 mmol) and stir for 48 hours. Dilute with ether, wash with water (2×), wash with 1N aqueous hydrochloric acid (2×), dry over anhydrous sodium sulfate, filter, and concentrate the solution. Purify the residue on silica eluting with 50 to 100% ethyl acetate/hexanes over 25 minutes to obtain the title compound as a white solid (254 mg, 40%). LC-MS m/z 385.0 (M⁺−I).

EXAMPLE 42

N-{3-[5-Fluoro-1-(3-methylamino-propyl)-indan-1-yl]-1H-indol-7-yl}-methanesulfonamide

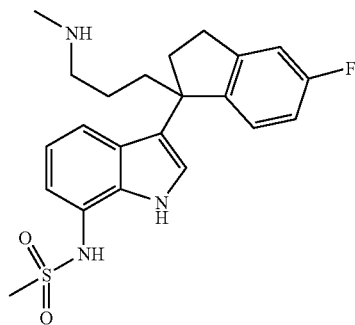

Stir N-{3-[5-fluoro-1-(3-iodo-propyl)-indan-1-yl]-1H-indol-7-yl}-methane sulfonamide (88 mg, 0.17 mmol) and methylamine (40% in water, 2 ml) in tetrahydrofuran (1 ml) at room temperature under nitrogen for 30 minutes. Dilute with dichloromethane and 10% aqueous potassium carbonate. Filter the white solids that crush out and dry under high vacuum to obtain the title compound (35 mg, 49%). LC-MS m/z 416.1 (M⁺+1).

EXAMPLE 43

N-{3-[1-(3-Dimethylamino-propyl)-5-fluoro-indan-1-yl]-1H-indol-7-yl}-methanesulfonamide

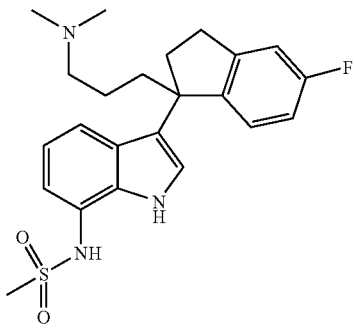

Stir N-{3-[5-fluoro-1-(3-iodo-propyl)-indan-1-yl)]-1H-indol-7-yl}-methane sulfonamide (65 mg, 0.13 mmol) and dimethyl amine (5.0 ml, 2.0 M in tetrahydrofuran) at room temperature under nitrogen overnight. Remove the volatiles under high vacuum, dissolve the residue in dichloromethane, wash with saturated aqueous sodium bicarbonate, dry over anhydrous sodium sulfate, filter, and concentrate in vacuo. Purify the residue on silica eluting with 10% methanol in dichloromethane to obtain the title compound as a white solid (34 mg, 65%). LC-MS m/z 430.2 (M⁺+1).

EXAMPLE 44

N-{3-[5-Fluoro-1-(3-morpholin-4-yl-propyl)-indan-1-yl]-1H-indol-7-yl}-methanesulfonamide

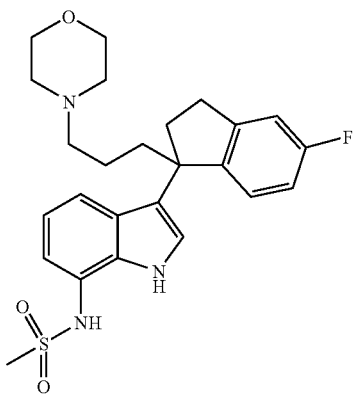

Combine N-{3-[5-fluoro-1-(3-iodo-propyl)-indan-1-yl]-1H-indol-7-yl}-methane sulfonamide (65 mg, 0.13 mmol) and morpholine (2 ml) in anhydrous tetrahydrofuran (2.5 ml) and stir at room temperature under nitrogen overnight. Remove the volatiles under high vacuum, dissolve the residue in dichloromethane, add solid potassium carbonate, stir for ten minutes, filter, and concentrate in vacuo. Purify the residue on silica eluting with 5 to 10% methanol in dichloromethane over 15 minutes to obtain the title compound as a white solid (50 mg, 83%). LC-MS m/z 472.2 (M$^+$+1).

What is claimed is:

1. A compound of the formula:

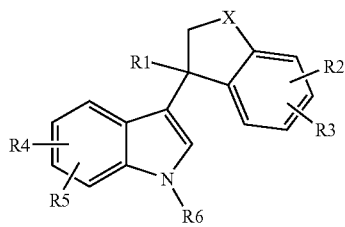

Formula I wherein,

X represents —CH$_2$—, —CH$_2$CH$_2$— or —CH$_2$O—;

R$^1$ represents hydrogen, (C$_1$-C$_4$)alkyl, (C$_3$-C$_7$)cycloalkyl, hydroxy(C$_1$-C$_4$)alkyl, halo(C$_1$-C$_4$)alkyl, (C$_1$-C$_4$)alkyl-heterocycle, (C$_1$-C$_4$)alkyl-NH(C$_1$-C$_4$)alkylamine, or (C$_1$-C$_4$)alkyl-N,N-(C$_1$-C$_4$)dialkylamine;

R$^2$ represents hydrogen, halo, (C$_1$-C$_4$)alkyl, heterocycle, or substituted heterocycle;

R$^3$ represents hydrogen, halo, (C$_1$-C$_4$)alkyl, heterocycle, or substituted heterocycle;

R$^4$ represents NHSO$_2$CH$_3$;

R$^5$ represents hydrogen;

R$^6$ represents hydrogen or (C$_1$-C$_4$)alkyl;

R$^7$ represents (C$_1$-C$_4$)alkyl, aryl, NH(C$_1$-C$_4$)alkylamine, or N,N-(C$_1$-C$_4$)dialkylamine;

R$^8$ represents (C$_1$-C$_4$)alkyl, (C$_1$-C$_4$)alkoxy, or aryl(C$_1$-C$_4$)alkoxy;

R$^9$ represents (C$_1$-C$_4$)alkyl or (C$_1$-C$_4$)alkoxy, and

R$^{10}$ represents hydrogen, (C$_1$-C$_4$)alkyl, (C$_3$-C$_7$)cycloalkyl, or (C$_1$-C$_4$)alkyl-(C$_3$-C$_7$)cycloalkyl, or a pharmaceutically acceptable salt thereof.

2. The compound according to claim 1 wherein X represents —CH$_2$— or —CH$_2$CH$_2$—.

3. The compound according to claim 1 wherein X represents —CH$_2$O—.

4. The compound according to claim 1 wherein R$^1$ represents hydrogen, methyl, ethyl, propyl, isopropyl, (C$_3$-C$_7$)cycloalkyl, hydroxy(C$_1$-C$_4$)alkyl, halo(C$_1$-C$_4$)alkyl, (C$_1$-C$_4$)alkyl-heterocycle, (C$_1$-C$_4$)alkyl-NH(C$_1$-C$_4$)alkylamine, or (C$_1$-C$_4$)alkyl-N,N-(C$_1$-C$_4$)dialkylamine.

5. The compound according to claim 4 wherein R$^1$ represents methyl, ethyl, propyl, isopropyl, (C$_3$-C$_7$)cycloalkyl, hydroxy(C$_1$-C$_4$)alkyl, halo(C$_1$-C$_4$)alkyl, (C$_1$-C$_4$)alkyl-heterocycle, (C$_1$-C$_4$)alkyl-NH(C$_1$-C$_4$)alkylamine, or (C$_1$-C$_4$)alkyl-N,N-(C$_1$-C$_4$)dialkylamine.

6. The compound according to claim 1 wherein R$^2$ represents hydrogen, halo, methyl, ethyl, propyl, isopropyl, heterocycle, or substituted heterocycle.

7. The compound according to claim 6 wherein R$^2$ represents hydrogen, fluoro, chloro, bromo, methyl, ethyl, propyl, or isopropyl.

8. The compound according to claim 1 wherein R$^3$ represents hydrogen, fluoro, chloro, or bromo.

9. The compound according to claim 8 wherein R$^3$ represents hydrogen or fluoro.

10. The compound according to claim 1 wherein R$^6$ represents hydrogen, methyl, or ethyl.

11. A pharmaceutical composition comprising the compound according to claim 1 in combination with a pharmaceutically acceptable carrier, diluent, or excipient.

12. A compound selected from the group consisting of N-[3-(1-Ethyl-5-fluoro-indan-1-yl)-1H-indol-7-yl]-methanesulfonamide, N-[3-(6-Fluoro-1-methyl-1,2,3,4-tetrahydro-naphthalen-1-yl)-1H-indol-7-yl]-methanesulfonamide, N-[3-(6,8-Difluoro-1-methyl-1,2,3,4-tetrahydro-naphthalen-1-yl)-1H-indol-7-yl]-methanesulfonamide, N-[3-(4-Ethyl-7-fluoro-chroman-4-yl)-1H-indol-7-yl]-methanesulfonamide, and N-[3-(1-Cyclopropyl-5-fluoro-indan-1-yl)-1H-indol-7-yl]-methanesulfonamide, a pharmaceutically acceptable salt thereof.

* * * * *